US007282368B2

(12) United States Patent
Toh et al.

(10) Patent No.: US 7,282,368 B2
(45) Date of Patent: Oct. 16, 2007

(54) METHOD FOR DIAGNOSING AND MONITORING HEMOSTATIC DYSFUNCTION, SEVERE INFECTION AND SYSTEMATIC INFLAMMATORY RESPONSE SYNDROME

(75) Inventors: Cheng Hock Toh, Liverpool (GB); Liliana Tejidor, Raleigh, NC (US); Mike Neisheim, Kingston (CA); Gregory Jones, Hillsborough, NC (US)

(73) Assignee: bioMerieux, Inc., Durham, NC (US)

( * ) Notice: Subject to any disclaimer, the term of this patent is extended or adjusted under 35 U.S.C. 154(b) by 545 days.

(21) Appl. No.: 10/375,251

(22) Filed: Feb. 27, 2003

(65) Prior Publication Data

US 2003/0228625 A1 Dec. 11, 2003

Related U.S. Application Data

(60) Provisional application No. 60/404,652, filed on Aug. 20, 2002, provisional application No. 60/396,392, filed on Jul. 17, 2002, provisional application No. 60/363,073, filed on Mar. 11, 2002, provisional application No. 60/359,932, filed on Feb. 27, 2002.

(51) Int. Cl.
*G01N 33/92* (2006.01)
*G01N 33/68* (2006.01)

(52) U.S. Cl. ............................. 436/71; 436/63; 436/86
(58) Field of Classification Search ................. 436/86, 436/63, 71; 435/7.1
See application file for complete search history.

(56) References Cited

U.S. PATENT DOCUMENTS

| 6,133,039 | A | * | 10/2000 | Heinecke | 436/89 |
| 6,429,017 | B1 | * | 8/2002 | Toh et al. | 436/69 |
| 6,642,055 | B1 | * | 11/2003 | Arbogast | 436/88 |
| 6,898,532 | B1 | * | 5/2005 | Toh et al. | 702/22 |
| 2002/0150534 | A1 | | 10/2002 | Yu et al. | |
| 2002/0193949 | A1 | * | 12/2002 | Fischer et al. | 702/22 |

FOREIGN PATENT DOCUMENTS

| WO | WO 96/41291 | 12/1996 |
| WO | WO 00/46603 | 8/2000 |
| WO | WO 01/96864 | 1/2001 |
| WO | WO 02/341110 | 5/2002 |

OTHER PUBLICATIONS

PCT International Search Report mailed Jun. 12, 2003, International application No. PCT/US03/05980.

Deguchi et al., "Cardiolipin is a Normal Component of Human Plasma Lipoproteins", *Proc. Natl. Acad. Sci. USA*, 97: 1743-1748 (2000).
Downey et al., "Novel and Diagnostically Applicable Information from Optical Waveform Analysis of Blood Coagulation in Disseminated Intravascular Coagulation", *Br. J. Haem.*, 98: 68-73 (1997).
Downey et al., "Early Identification and Prognostic Implications in Disseminated Intravascular Coagulation Through Transmittance Waveform Analysis", *Thromb. Haemost.*, 80: 65-69 (1998).
Galan et al., "Preparations of Synthetic Phospholipids Promote Procoagulant Activity on Damaged Vessels: Studies Under Flow Conditions", *Transfusion*, 38: 1004-1010 (1998).
Higgins, D. L. et al., "Lipid Mobility in the Assembly and Expression of the Activity of the Prothrombinase Complex", *J. Biol. Chem.*, 260: 3604-3612 (1985).
Meers et al., "Calcium-Dependent Annexin V Binding to Phosphoipids: Stoichiometry, Specificity, and the Role of Negative Charge", *Biochemistry*, 32: 11711-21 (1993).
Moyer, M. P. et al, "Plasma Lipoproteins Support Prothrombinase and Other Procoagulant Enzymatic Complexes", *Arterioscler. Throm. Vasc. Biol.*, 18: 458-465 (1998).
Nesheim, M. E. et al., The Contribution of Bovine Factor V and Factor Va to the Activity of Prothrombinase, *J. Biol. Chem.*, 254: 10952-10956 (1979).
Ran, S., "Increased Exposure of Anionic Phospholipids on the surface of Tumor Blood Vessels", *Cancer Res.*, 62: 6132-6140 (2002).
Rosing, J. et al., "Prothrombin Activation on Phospholipid Membranes with Positive Electrostatic Potential", *Biochemisty*, 27: 8-11 (1988).
Rota, S. et al., "Atherogenic Lipoproteins Support Assembly of the Prothrombinase Complex and Thrombin Generation: Modulation by Oxidation and Vitamin E", *Blood*, 91: 508-15 (1998).
Tait, et al., "Phospholipid Binding of Annexin V: Effects of Calcium and Membrane Phosphatidylserine Content", *Arch. Biochem. Biophys.*, 298: 187-91 (1992).
Taylor et al., "Towards Definition, Clinical and Laboratory Criteria, and a Scoring system for Disseminated Intravascular Coagulation", *Thromb, Haemost.*, 86: 1327-1330 (2001).
Toh et al., "Early Identification of Sepsis and Mortality Risks Through Simple, Rapid Clot-waveform Analysis", *Intensive Care Med.*, 29: 56-61 (2003).
PCT International Search Report mailed Jun. 12, 2003, International application No. PCT/US03/05980.

* cited by examiner

*Primary Examiner*—Maureen M. Wallenhurst

(57) ABSTRACT

A method for diagnosing and monitoring subjects for hemostatic dysfunction, severe infection and systematic inflammatory response syndrome is provided whereby lipoproteins are examined for abnormalities, particularly for prothrominase enhancement, through quantitative and qualitative analysis.

6 Claims, 21 Drawing Sheets

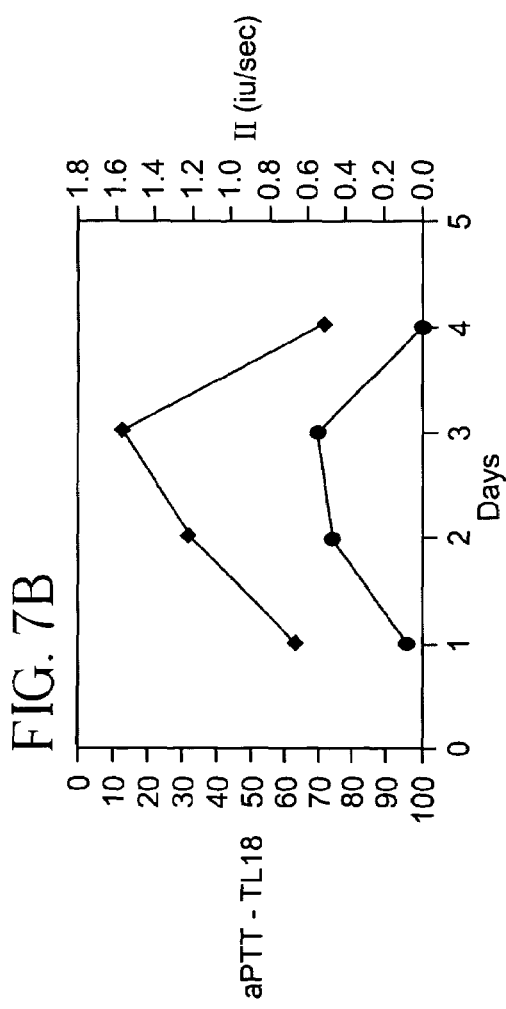
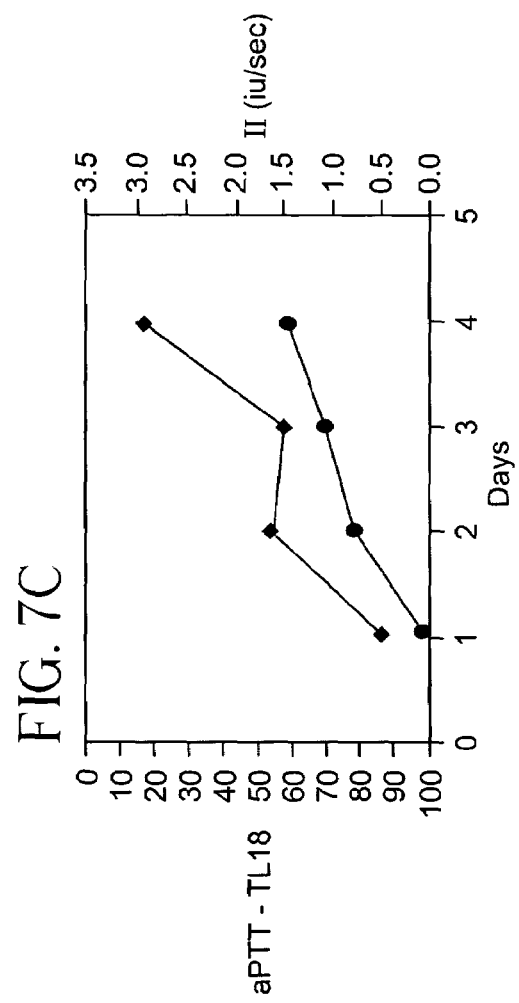

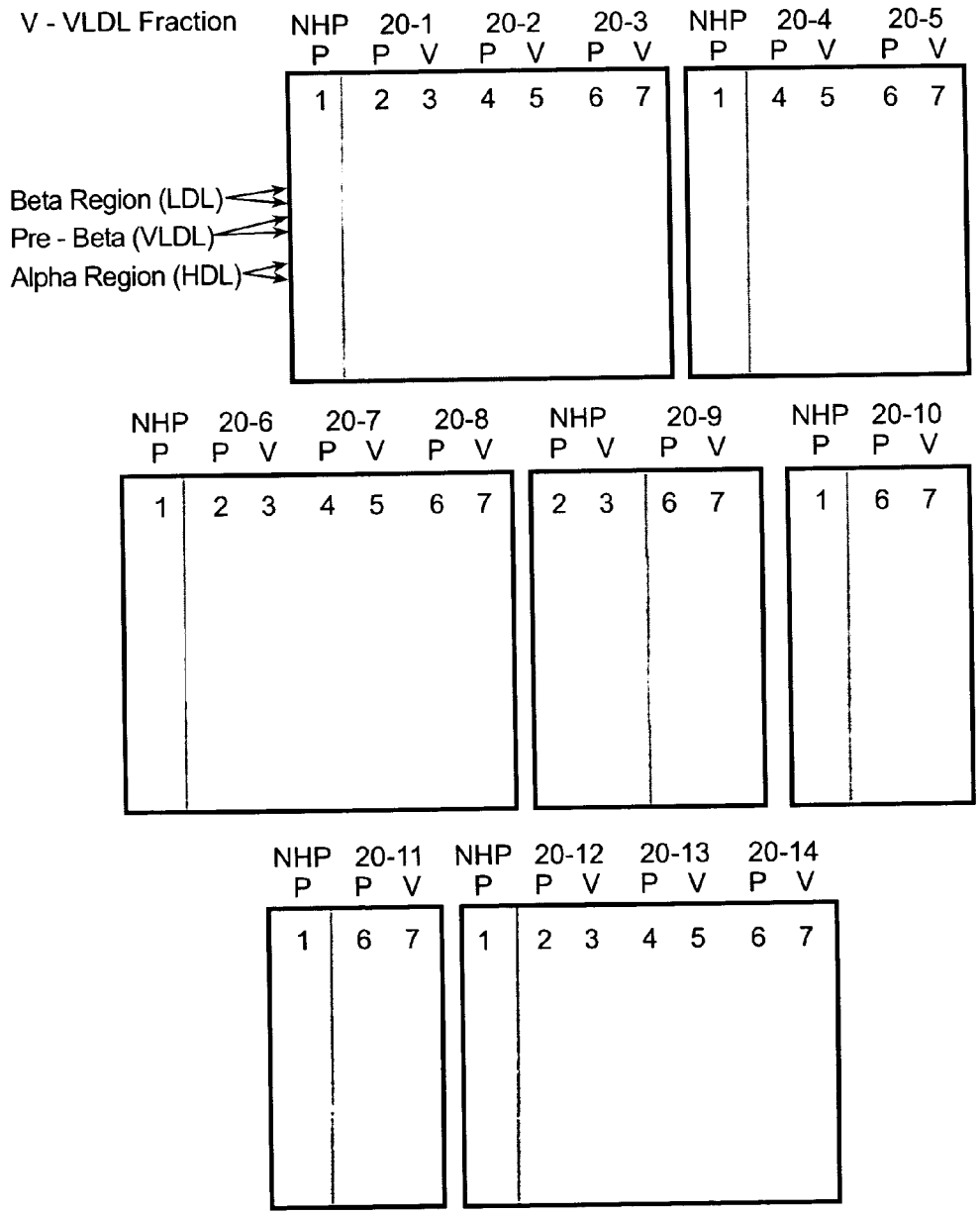
FIG. 12B  Agarose Gel Electrophoresis of Patient Plasma and Isolated VLDL

METHOD FOR DIAGNOSING AND MONITORING HEMOSTATIC DYSFUNCTION, SEVERE INFECTION AND SYSTEMATIC INFLAMMATORY RESPONSE SYNDROME

FIELD OF INVENTION

This application claims priority from U.S. Provisional Patent Appls. Ser. No. 60/359,932 (filed Feb. 27, 2002), Ser. No. 60/363,073 (filed Mar. 11, 2002), Ser. No. 60/396,392 (filed Jul. 17, 2002) and Ser. No. 60/404,652 (filed Aug. 20, 2002).

BACKGROUND OF THE INVENTION

Severe infection and sepsis are common causes of morbidity and mortality. Sepsis is a vast clinical entity that takes many forms. The pathophysiology of a host response to infection is complex and the signs and symptoms of systemic inflammation may have an infectious or non-infectious etiology and are not specific. Patients with systemic infection are often difficult to distinguish from patients with similar clinical signs and laboratory findings without infection. Infection has multiple causes including that caused by bacterium, fungi, parasites and viruses.

Bacteriological evidence of infection may not develop at the same time as clinical signs of distress. Further, it requires time to grow a culture of organism from a blood sample to confirm the presence of infective bacteria and the results may be incorrect due to contamination, etc. As used herein, severe infection may include a diagnosis of sepsis, severe sepsis, septicaemia, and septic shock as well as disseminated intravascular coagulation ("DIC"). Also included in the definition of infection is systemic inflammatory response syndrome "SIRS" although it may have infectious as well as non-infectious origin (both of which are encompassed herein). SIRS may exhibit or develop into systemic inflammation that ultimately leads to multiple organ dysfunction syndrome. Patients with SIRS may develop the syndrome from infection, trauma, burns, pancreatitis, etc.

As used herein hemostatic dysfunction may be defined as an error in coagulation. For both DIC and sepsis, there is increasing recognition of common and overlapping pathophysiological pathways that link inflammation and coagulation. The recent therapeutic success of recombinant human activated protein C (APC) in severe sepsis especially after a myriad of unsuccessful strategies would support this further. APC suppresses thrombin generation via the inactivation of coagulation co-factors, Va and VIIIa and is also thought to have anti-inflammatory properties.

There is a continuing need to find early indicators or markers of infection, SIRS and hemostatic dysfunction due to lack of specificity of current methods of diagnosis. An early diagnosis may greatly increase recovery of the patient and reduce the morbidity and mortality rates associated with this population. Further a diagnostic marker or test to monitor the efficacy of treatment of the host response to infection, SIRS and hemostatic dysfunction is needed as well.

The time dependent measurement profiles of coagulation screening assays have been associated with predicting congenital, acquired imbalances and hemostatic dysfunction as described in Givens et al. WO 96/41291 and Toh et al. WO 00/46603. Once such profile is that of an activated partial thromboplastin time ("APTT") assay having a decrease in plasma light transmittance before clot formation, now commonly referred to as a biphasic waveform (also referred to herein as BPW). This BPW has been associated with critically ill patients having DIC which is common in many primary diseases including sepsis. The biphasic waveform on coagulation instruments offers a simple and rapid test for early diagnosis of hemostatic dysfunction, including DIC.

As described in WO 01/96864 (Dec. 20, 2001), a calcium-dependent complex between C reactive protein (CRP) and lipoprotein (particularly very low density lipoprotein (VLDL)) has been identified as the molecular mechanism underlying the biphasic waveform. The complex may be used to identify patients with sepsis, SIRS and septicaemia in addition to patients with other hemostatic dysfunction that can lead to bleeding or thrombosis including DIC. Further, WO 01/96864 describes detecting the complex by a clotting assay, latex agglutination or gold sol assay, and immunoassay whereby the precipitate is formed prior to or in the absence of clot formation, depending on the reagent used.

While the biphasic waveform and the CRP-lipoprotein complex provide advances in the early diagnosis of different kinds of severe infection and haemostatic dysfunction (including DIC and sepsis), there is a continued need to further identify early diagnostic means, particular markers severe infection, SIRS and hemostatic dysfunction.

SUMMARY OF THE INVENTION

It has been discovered that diagnosis and monitoring of a host response to severe infection, SIRS and hemostatic dysfunction may be accomplished by detecting qualitative and quantitative differences between lipoproteins of this population as compared with lipoproteins found in normal, healthy samples.

In one preferred embodiment, a method for diagnosis and monitoring severe infection, SIRS and hemostatic dysfunction has been found said method comprising (a) obtaining a patient sample; (b) measuring a lipoprotein fraction from said sample for an abnormality; and (c) correlating said lipoprotein measurement to an abnormality found in patients having severe infection, SIRS or hemostatic dysfunction. Further, said method can be utilized to predict an increased likelihood of system failure or mortality in said patient.

Another aspect of the invention is a method for predicting an increased likelihood of infection (particularly sepsis) in a patient, comprising: (a) obtaining a sample of very large density lipoproteins (VLDLs) from a patient; and (b) determining the activity of VLDLs in said sample for activating prothrombin; a greater activity of said VLDLs for activating prothrombin indicating an increased likelihood of infection in said patient. The determining step may be carried out directly or indirectly by any suitable means, such as by measuring rate of thrombin generation.

In yet another aspect of the invention, the method for diagnosing severe infection, SIRS or hemostatic dysfunction is accomplished by steps comprising (a) obtaining a patient sample; (b) subjecting the patient sample to a biphasic waveform screening test to obtain a normal or biphasic waveform result; (c) subjecting said patient samples demonstrating said biphasic waveform result to a lipoprotein analysis; and (d) comparing said lipoprotein analysis with that of a normal sample to diagnosis of severe infection, SIRS or hemostatic dysfunction.

In yet another aspect of the invention, a method for diagnosing severe infection is accomplished by the steps comprising (a) obtaining a sample from a patient; (b) measuring said sample lipoprotein fraction for binding specificity with Annexin V; and (c) correlating said binding specificity prothrombin activation with the diagnosis and/or monitoring of a host response to severe infection, including SIRS, DIC and sepsis. Further, said method can be utilized to predict an increased likelihood of system failure or mortality in said patient.

BRIEF DESCRIPTION OF THE DRAWINGS

FIGS. 7A-C illustrate total triglyceride levels where (A) shows the difference in plasma triglyceride concentrations between normal individuals (x), patients with normal waveforms (+) and biphasic waveforms at different APTT-TL18 values (◇). (B) and (C) shows time courses from 2 patients who recover and die from sepsis, respectively, in terms of total prothrombinase activity (♦), as calculated by the product of plasma triglyceride and the specific prothrombinase activity/mM triglyceride, and APTT-TL18 values (●).

FIGS. 12A-B provide a serial sample profile of slope-1 values for a representative patient (A) and the corresponding agarose gel electrophoresis of patient's plasma and isolated VLDL (B).

DETAILED DESCRIPTION

Figure 1A:
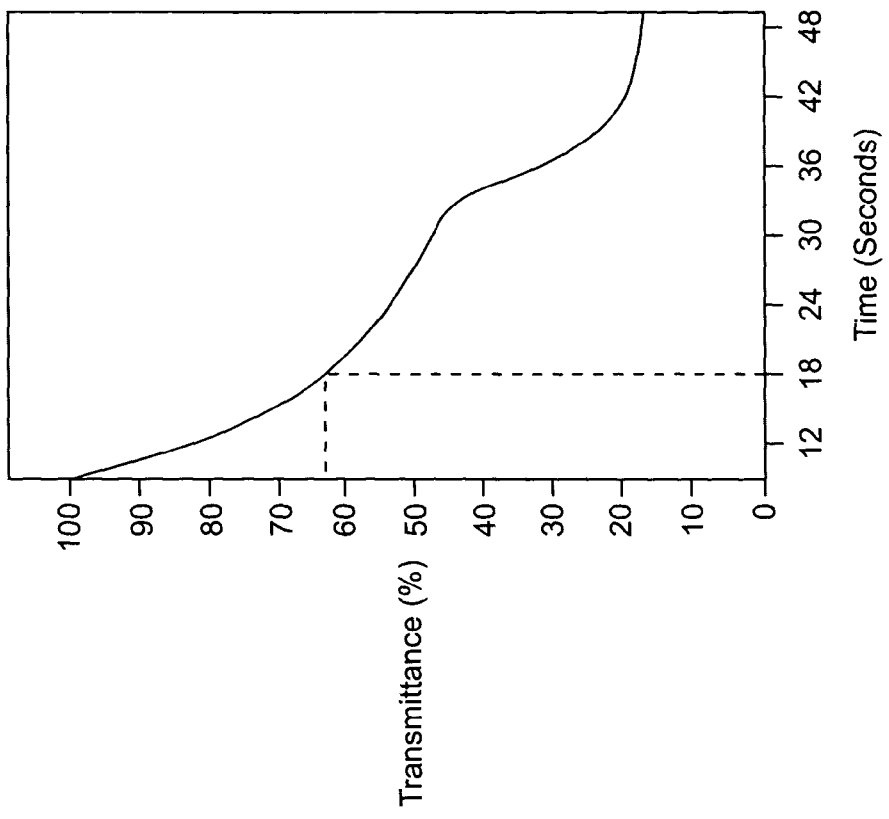
FIG. 1 illustrates a normal waveform at 580 nm (panel A) and a decrease in light transmission prior to formal clot formation to produce a biphasic waveform profile (panel B) where the dashed line denotes transmittance level at 18 seconds (TL 18) as the quantitative index, in A, TL18=100 and in B, TL18=63.

Although the lipoprotein-acute phase protein complex (typically referred to as CRP-VLDL) formed in-vivo has been described in patients having infection and sepsis, the measurement of quantitatively and qualitatively differentiating the lipoprotein subfraction separate from the complex substrate not been previously associated with infection, SIRS, sepsis or hemostatic dysfunction. It has been discovered that the lipoprotein fractions of patients with severe infection, SIRS and hemostatic dysfunction are distinguishable from those of normal patients and thus the lipoprotein itself may be used as a biomarker to diagnose and monitor these disease states. The differences in the lipoprotein of this population is not limited to just that lipoprotein fraction that forms the complex. Disturbances in these lipoprotein subclasses influence complex formation and may also be determinants of clinical outcome.

The step of obtaining lipoproteins from patient samples may be carried out by any suitable means, such as by collecting a blood sample from a patient and then utilizing a means to examine (quantitative or qualitative) of the abnormal lipoproteins found in patients with severe infection, SIRS and hemostatic dysfunction.

Still further, separating the abnormal lipoproteins may not be required if a specific binding assay is utilized, wherein said assay may be competitive or non-competitive. In such assays, a component may be designed that binds directly or indirectly to a part or all of the lipoprotein anomalies found in patients with severe infection, SIRS and hemostatic dysfunction, particularly sepsis and DIC, thus a patient sample (sample is defined herein to include plasma, whole blood sample, serum, etc.) may be directly analysed for the anomaly relating to the lipoprotein. More preferably, the assay may be a clotting assay, latex agglutination or gold sol assay, ligand assay, protein binding assay or immunoassay. More preferably serum or plasma is utilized as the patient sample, most preferably plasma. In one preferred assay, surface changes of the abnormal lipoprotein are measured by the lipoprotein binding to Annexin 5 (or another specific ligands that recognize anionic phospholipids), either directly or indirectly. If preferred, the lipoprotein may be subfactionated into VLDL, IDL and LDL. Futher, antibodies (or fragments thereof) specific to Annexin 5 may be prepared and utilized in a specific binding assay such that the abnormal lipoproteins are detected and thereafter correlated with patients having severe infection, SIRS or hemostatic dysftnction, particularly those with DIC or sepsis.

More particularly, according to the invention, provided is a diagnostic method for host response to infection, SIRS or hemostatic dysfunction, more preferably for sepsis and DIC, whereby an in-vivo circulating complex of lipoproteins is identified as abnormal. Preferably the method is specific to beta lipoproteins (apoB containing lipoproteins), particularly those of the same buoyant density including very low density lipoprotein (VLDL), low density lipoprotein (LDL), and intermediate density lipoprotein (IDL). More preferably anionic phospholipids are examined for abnormalities and most preferably VLDL is examined. The method may be used for predicting the prognosis of a patient as well as monitor the patient once therapy is initiated. The testing of the lipoproteins may be manual or automated and may include NMR analysis. More particularly, current chemistry tests for measuring cholesterol and triglycerides (TG) are independent of particle concentrations. By use of NMR technology, the core lipids (TG or cholesterol esters) do not impact particle concentration measurements. NMR gives a total number of particles of a certain size, thus allowing for calculation of total surface area whereas current chemistry tests assume that the TG are found solely in the VLDL size particles and LDL size particles are assumed to contain mainly cholesterol esters. Traditional chemistry tests for lipoproteins do not give information on the particle numbers and surface areas. According to one of the embodiments of this invention, these differences of particle numbers and surface areas of lipoproteins may be associated with severe infection including DIC and sepsis.

More particularly, it has been discovered that patients with severe infection, SIRS and hemostatic dysfunction have pro-coagulant lipoproteins referred to as "abnormal" lipoproteins herein. The changes in the lipoproteins are believed to be abnormal due to their metabolism. According to the invention, the lipoprotein changes may manifest in changes in physical properties as well as qualitative functional changes including an increase in procoagulant activity and enhanced prothrombinase activity. Lipoprotein changes that may be measured to develop a relationship between abnormal patient samples (from those having severe infection, SIRS or hemostatic dysfunction, particularly sepsis and DIC) and normal patient samples include the following: a shift in VLDL, IDL, LDL or high density lipoprotein (HDL) protein levels; increased surface exposed of anionic phospholipids (more preferably phospholipid phosphatidylserine (PS)); shift in VLDL size; shift in VLDL lipids (core and surface); shift in VLDL charge; appearance of procoagulant lipoproteins; indication of lipoprotein cascade disruption (drop in all lipoprotein concentrations), mildly elevated or depressed VLDL levels; depressed LDL levels; appearance of SAA-HDL; post-translational changes; lipoprotein assembly constituent changes; lipoprotein mobility changes; secretion changes; perfusion; lipoprotein enzyme changes (CETP, LCAT, etc.); lipoprotein receptor changes, indicator of lipoprotein oxidation, and endotoxin incorporation. In one preferred embodiment the abnormal lipoprotein detected and associated with severe infection, SIRS and hemostatic dysfunction, more preferably sepsis and DIC, is the lipoproteins with enhanced ability to support prothombinase activity (particularly VLDL). Additionally, in one preferred embodiment, the abnormal lipoproteins of patients with severe infection, SIRS and hemostatic dysfunction (more preferably with sepsis or DIC) may be identified by using various methods including measuring specifc apolipoproteins, partile sizes, numbers or lipids. More particularly, it involves the total surface area of lipoproteins relative to normals.

Thrombin generation in vivo is considered to be a pivotal process in DIC and markers of its generation increase during disease progression. For the enzymatic conversion of prothrombin to thrombin to occur at physiologically relevant rates, the components must be localised to appropriate surfaces. For in vivo, this is presumed to be supplied by activated platelets, mononuclear and perturbed endothelial cells. VLDL, at physiological levels, can also support relevant rates of thrombin generation and this is thought to be of relevance to the significant prediction of triglycerides to cardiovascular events. According to the invention, it has been discovered that CRP-VLDL is more than just a marker or predictor of DIC and that it exists in vivo with a possible pathogenic role through the ability to enhance and sustain the generation of thrombin.

Thrombin, as the main effector protease of the coagulation cascade, is of pivotal importance in the pathogenesis of DIC. Its procoagulant effect in converting fibrinogen to fibrin and its anticoagulant facilitation from binding to endothelial thrombomodulin to activate the protein C can be disregulated in DIC. According to the invention, it has been discovered that this enhanced procoagulant aspect of the VLDL from patients with the biphasic waveform may demonstrated through the significant shortening of clot time in a modified APTT assay. It has also been found that the added normal or patient VLDL provided the only differentiating source of phospholipid surface provision for the coagulation reaction. While not wishing to be bound by theory, this demonstration may also be one explanation for the finding that shorter APTT clot times are associated with adverse outcomes in a general hospital setting.

Still further, the invention may be practiced utilizing APTT parameters of waveform technology such as rate and/or acceleration. Also, the global coagulability assays and methods as taught in WO 02/34110 may be utilized to capture lipoprotein abnormalities in patients having severe infection, SIRS and hemostatic dysfunction. For example the detection of abnormal lipoprotein step may be carried out by detecting an enhanced procoagulant aspect of the VLDL from patients with the biphasic waveform by measuring a shortening of clot time in a modified APTT assay or measuring clot formation or measuring increased rate of accelaration of clot formation in a dilute tissue factor based assay.

In one preferred embodiment of the invention, it has been discovered that patients with hemostatic dysfunction, SIRS and a host response to severe infection have a VLDL that can significantly enhance thrombin generation. Moreover, the calculation of total thrombin generating capacity from the quantitative and qualitative changes in VLDL within serial samples of patients with sepsis and DIC show a direct positive correlation with clinical progression. This supports the relevance of thrombin as a major player in the pathophysiology of sepsis. While its primary role may have been as part of the acute phase protective initial response, the protracted or enhanced response fuelled by VLDL procoagulant surfaces may lead to deleterious consequences.

According to the invention a biomarker is provided, said biomarker of increased prothrombinase potential to better target anticoagulant based therapies such as recombinant human APC in severe sepsis. Further provided is insight into mechanisms other than by way of microparticles and cell surfaces that can enhance and abnormally sustain thrombin generation in vivo in disease states. Although not wishing to be bound by theory, it is believed that the qualitative increase in thrombin generation is associated with a lipoprotein compositional change in response to severe infection, SIRS and hemostatic dysfunction, particularly sepsis and inflammation.

Figure 1B:
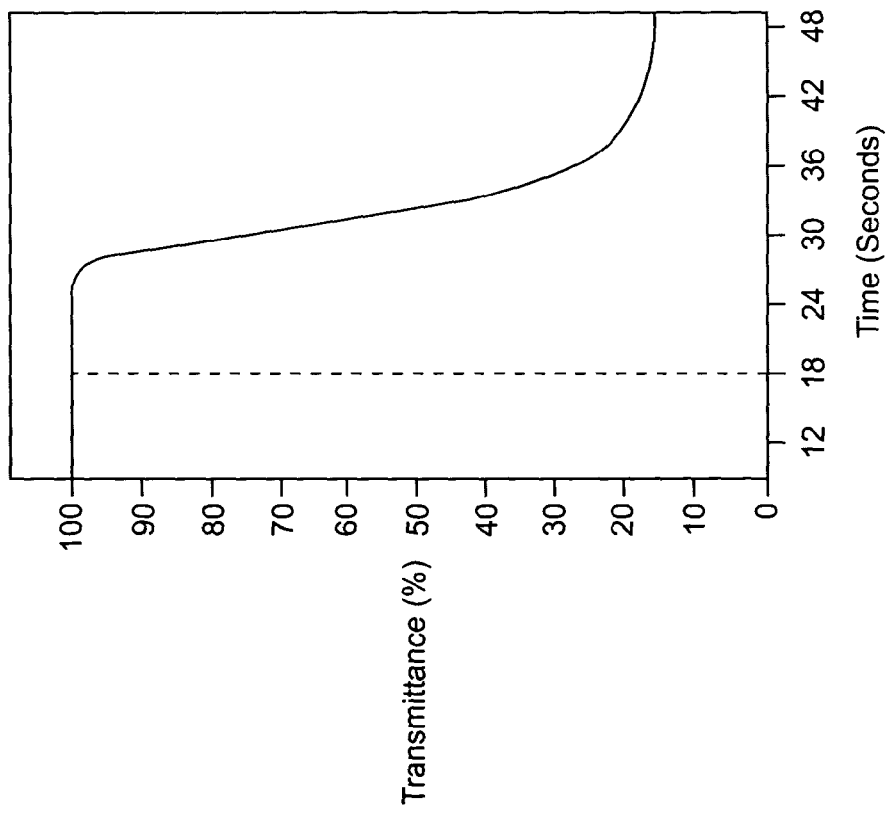
Figure 2:
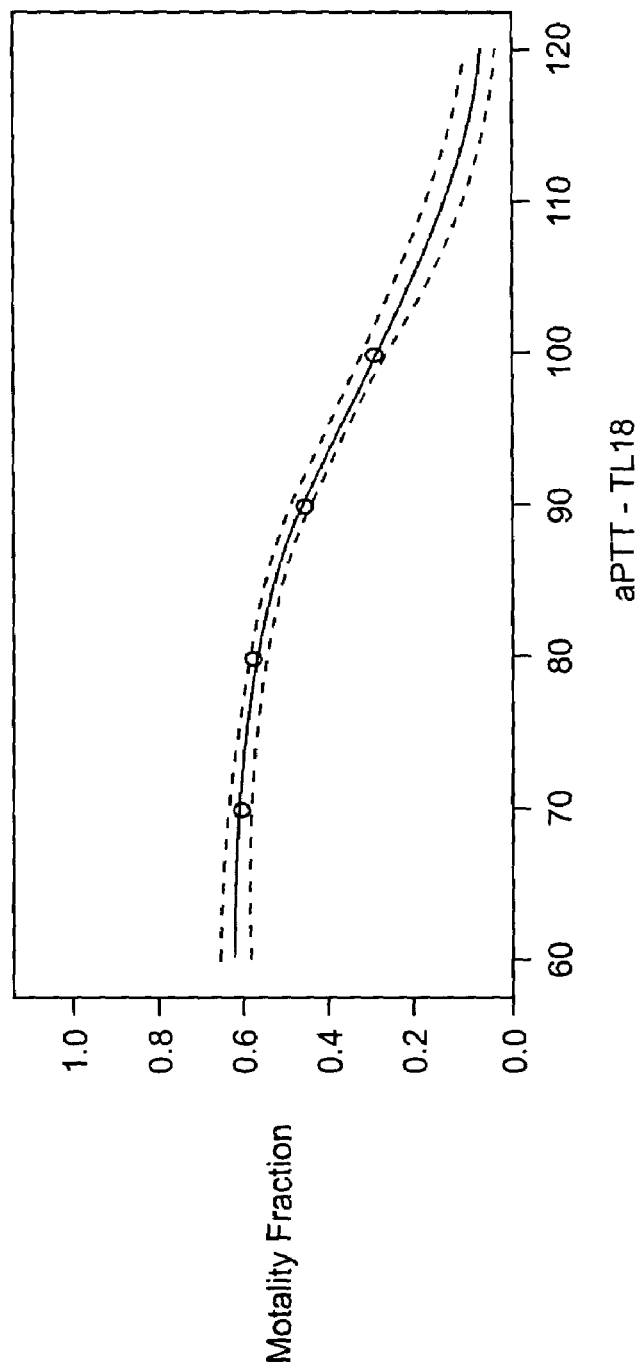
FIG. 2 shows logistic regression evaluation of the TL 18 data showing mortality fraction increasing from 0.26 in patients with a normal waveform to 0.61 when TL18 values reduced by 25-35%, with open circles= observed fractions; dashed lines=95% confidence limits.
Figure 3:
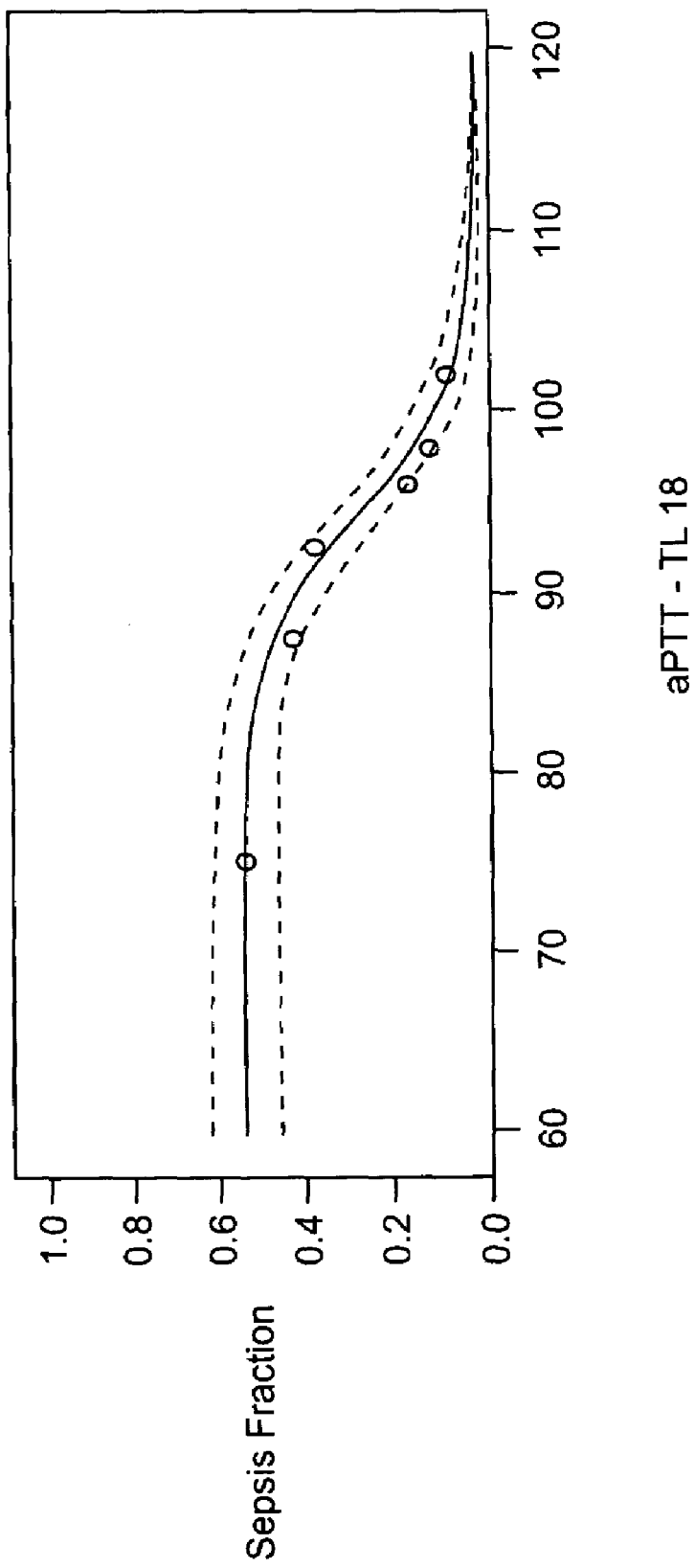
FIG. 3 shows the logistic regression evaluation of the TL18 data in the same cohort of patients for the association with sepsis with open circles= observed fractions, dashed lines=95% confidence limits.

In one preferred embodiment, the ability to support prothrombinase activity of the VLDL is measured. As used herein the ability to support prothrombinase activity also refers to and is used interchangeably with prothrombinase activity (PTase) and have been found to be altered in patients who have a biphasic waveform. Biphasic waveforms may be identified and measured by appropriate methods known to those skilled in the art utilizing coagulation assays and means for measuring the precoagulation phase (slope-1) over a time to provide a profile with determined normal and abnormal parameters. Preferably, an activated partial thromboplatin time (APTT) assay may be used with an optical transmittance coagulation analyzer, such as the MDA 180® (bioMerieux). For example, a normal waveform at 580 nm having a sigmoidal waveform pattern is characterized by an initial 100% light transmittance phase prior to formal clot formation as is illustrated in panel A of FIG. 1. In contrast, patients with a biphasic waveform (BPW) have an immediate, progressive fall in light transmittance that occurs even in the pre-clotting phase that affects the early part of the curve to produce a biphasic profile as is illustrated in panel B, FIG. 1. Patient populations with biphasic waveforms have been associated with higher mortality and sepsis incidence as depicted in FIGS. 2 and 3, respectively.

Accordingly to the invention, patients with a biphasic waveform have been observed to have at least about a two fold increase in specific PTase activity in lipoproteins (particularly VLDL) from biphasic waveform patients (e.g. patient in acute phase host response). The range of abnormality or increase in specific PTase activity (thrombin generating potention) of abnormal lipoprotein (particularly VLDL) of patients with severe infection, SIRS and hemostatic dysfunction may range from about two to about eight fold, more preferably from three to four fold, as compared with PTase activity of lipoproteins (particularly VLDL) from the normal, healthy population. It has been found that the total PTase mirrors APTT waveform (WF) changes. While not wishing to be bound by theory, it is believed that the enhanced PTase activity is due to increased anionic phospholipid exposure. Further the enhanced PTase is not believed to be due to platelet or endothelial microparticles apob presence on VLDL is believed to be important to PTase activity. Preferably, the PTase activity may be detected by a modified, more preferably with a modified coagulation assay such as APTT or modified tissue based assay. Preferably the assay to detect lipoprotein abnormality is carried out without forming a CRP-lipoprotein complex, more preferably a CRP-VLDL complex.

In another embodiment of the invention, it has been discovered that patients with severe infection, SIRS and sepsis (most preferably DIC) may be diagnosed by identification of an increased surface of negatively charged (anionic) phospholipid surface, particularly that of phospholipid phosphatidylserine (PS). While not wishing to be bound by theory, it is believed that the anionic phospholipid may be released from platelet microparticles which have demonstrable procoagulant activity in patients with sepsis. Similarly, the anionic phospholipid may be hepatically derived from membrane anionic phospholipid translocation or shedding in early endothelial dysfunction or apoptosis associated with multi-organ failure and IDC. Further, low expression of apolipoprotein E within the VLDL particles may substantially affect the uptake of remnant particle composition and may have relevance to their atherogenicity and their ability to support thrombin generation.

As known, the cell membrane PS is translocated to the outer layer of the membrane as one of the initial steps in apopotosis which mediates macrophage recognition and phagocytosis. PS is also crucial for coagulation reaction such as prothrombinase assembly. Therefore the increased thrombin generating potential of VLDL particles from patients with the CRP-VLDL complex is believed to be caused by an increase in exposed anionic phospholipid (including PS) sites on the particle surface, potentially absorbed onto the VLDL surface from apoptotic cells or by conformational change within the particles.

Annexin A5 (A5) is a calcium dependent phospholipid binding protein that has a high affinity for negatively charged phospholipid surfaces, with a higher specificity for PS than other anionic phospholipids. As previously described, specific binding assays may be prepared that take advantage of this binding affinity such that the abnormal lipoprotein of patients with severe infection, SIRS and hemostatic dysfunction may be measure utilizing A 5 as a labelled binding protein, antibodies to A5, etc., to detect the abnormal lipoproteins either directly or indirectly.

Figure 8A:
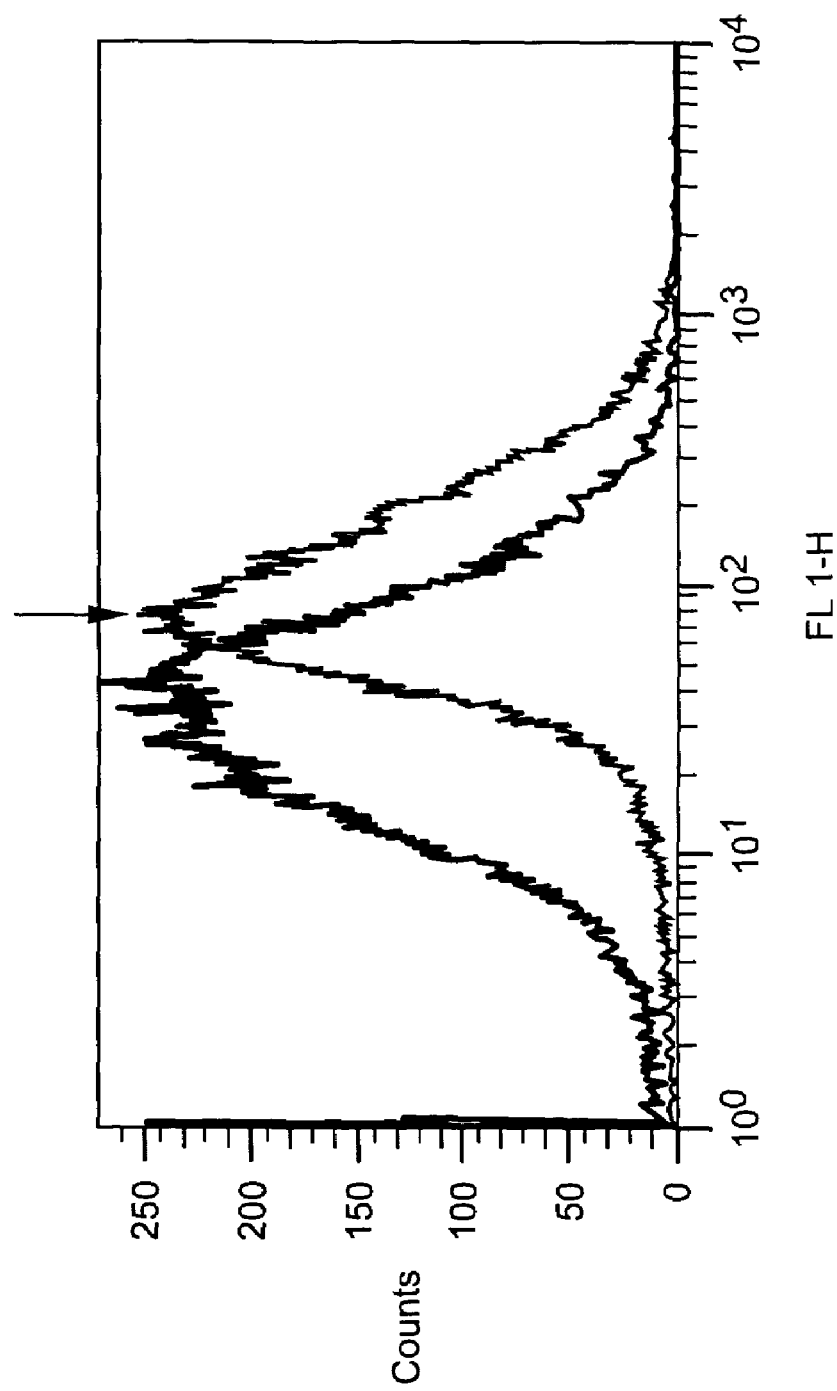
FIGS. 8A-C illustrate Annexin V studies. (A) shows the FACS plot comparing VLDL from normal and patient with the biphasic waveform (arrowed) following addition of fluorescent conjugated annexin V (B) illustrates the effect on prothrombinase activity by incubating increasing concentrations of annexin V with VLDL from norrnal individuals (open bars) and patients with the biphasic waveform (shaded bars) is shown. Data are mean±SEM; n=4 in each group (* p<0.01, ** p <0.002). (C) demonstrates the comparative effect of increasing annexin V (single line) or 9D2 antibody (dashed line) on prothrombinase activity in VLDL from normal (□) versus patient with the biphasic waveform (♦).
Figure 8B:
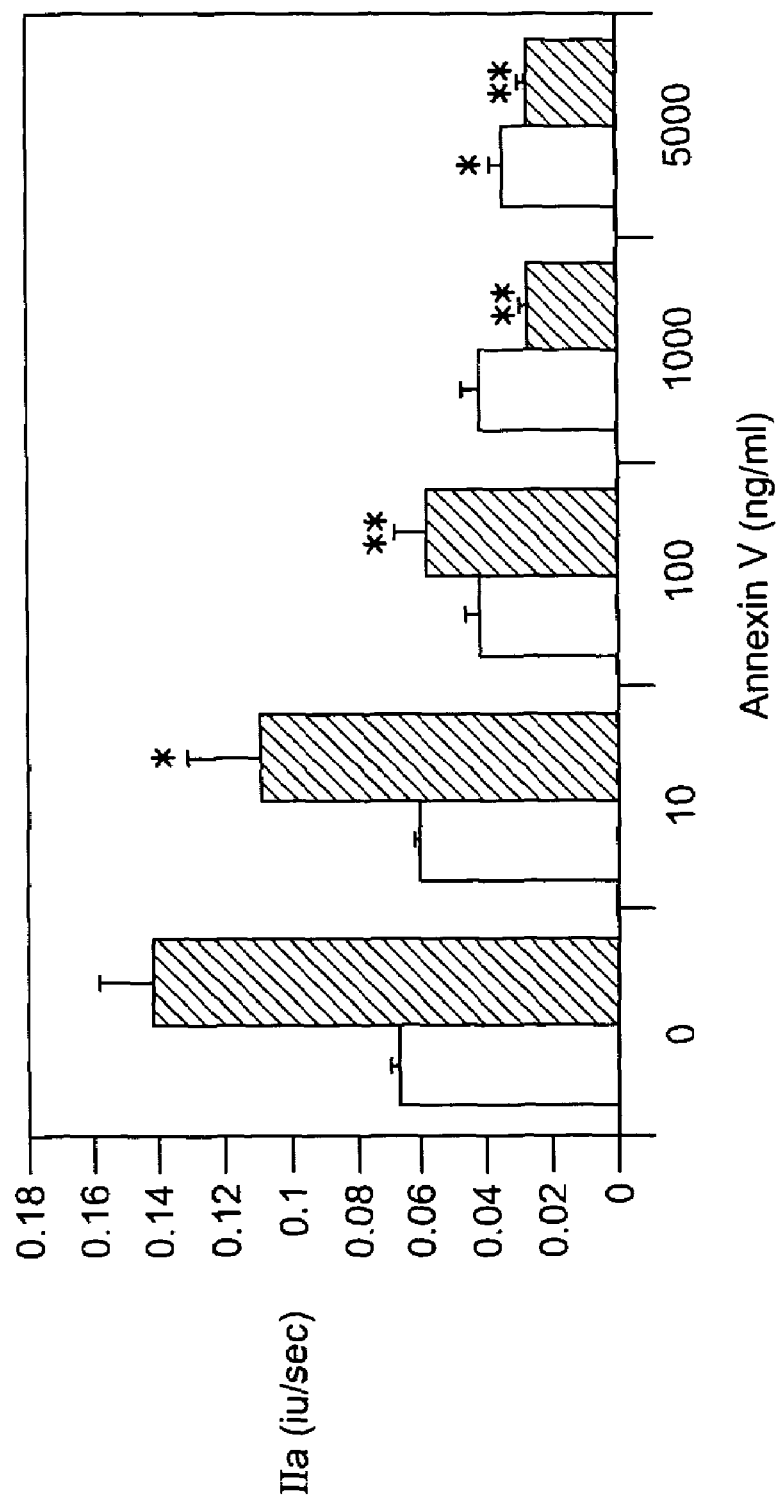
Figure 8C:
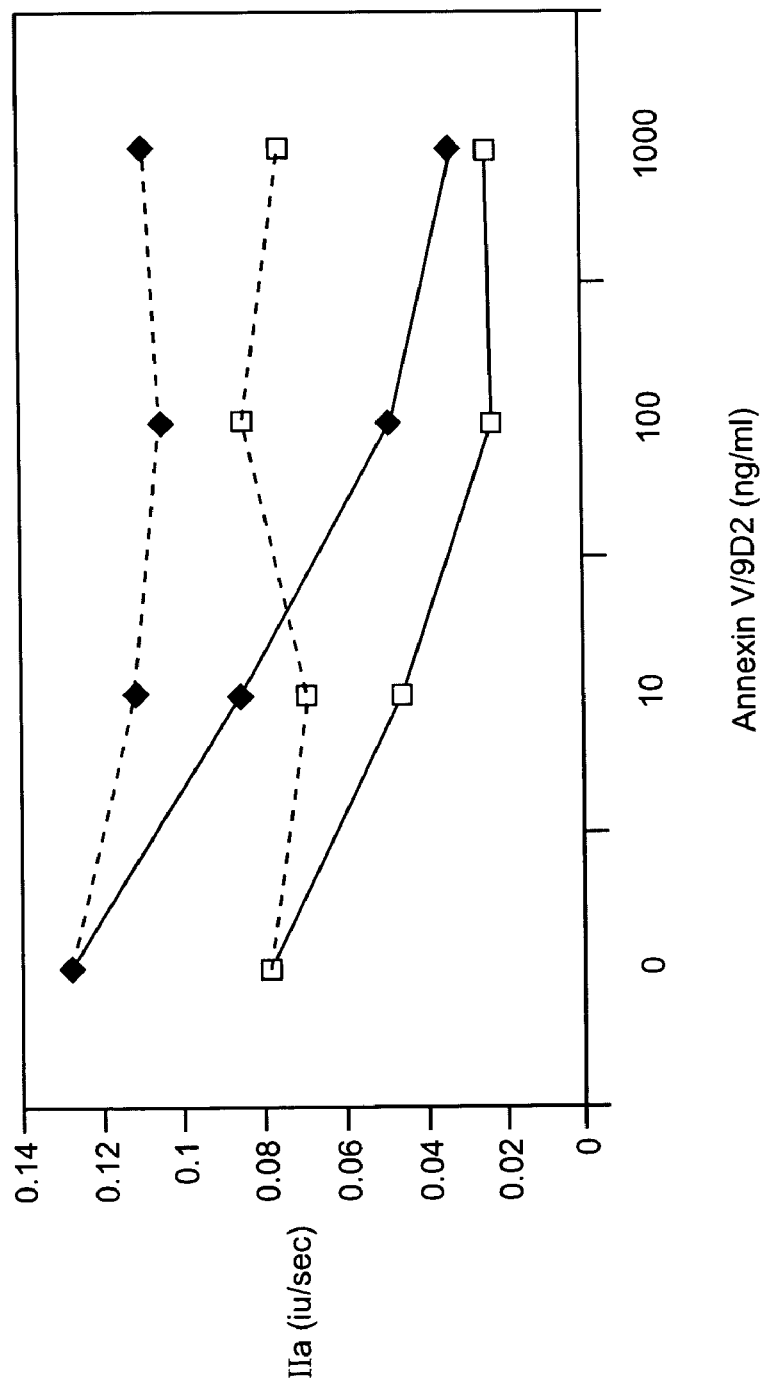

Accordingly to another embodiment of the present invention, it has been found that the A5 binding capacity may identify exposed anionic phosphoslipid sites and block the anionic phosphoslipid dependent reactions. As demonstrated in FIG. 8B, A5 inhibits prothombinase assembly. As depicted in FIG. 8B, the first bar shows normal patients treated with A5 and the second bar shows biphasic patients treated with A5 at varying concentrations of A5. Preferably the A5 is administered in an effective amount (preferably at least about 100 ng/ml, more preferably within the range of 100 to 5000 ng/ml) to re-equilibrate the hemostatic system of a biphasic patient with severe infection, DIC or sepsis. A5 has anticoagulant properties demonstrable in-vitro, and thus it is thought that to form an anti-thrombotic shield around exposed PS, prohibiting the formation of functional procoagulant complexes occurs. Anti-phospholipid antibodies putatively disrupt this shield thus explaining the prothrombotic tendency observed in these patients. Accordingly to the invention, A5 may be provided as a therapy for patients with clinical conditions associated with DIC because the therapeutic intervention could re-equilibrate the hemostatic system to impact upon the high mortality of this group.

The following non-limiting examples illustrate this invention.

EXAMPLES

Example 1

Methods

Clinical study

In a 24-month prospective study, APTT waveform analysis was performed on a daily basis in all consecutive adult patient admissions to the ITU of the Royal Liverpool University Hospital. The study was conducted to gain pathophysiological and mechanistic insight on clinical disease from when CRP-VLDL complexation is maximal. As such, the association of interest is between the lowest TL18 value; i.e. the most abnormal waveform in detecting maximal complex formation, as compared with its individual components (CRP or VLDL) for each individual patient episode with the diagnosis of DIC. DIC was defined according to the International Society of Thrombosis and Haemostasis Standardization Sub-Committee cumulative score of 5 or above, derived from changes in the platelet count, prothrombin time (PT), fibrinogen and D-dimer levels (Taylor, F. B., Toh, C. H., Hoots, W. K., Wada, H., Levi, M. 2001. Towards definition, clinical and laboratory criteria and a scoring system for disseminated intravascular coagulation. *Thromb.*

*Haemost.* 86:1327-1330). PT, fibrinogen and D-dimers were measured using Simplastin S, Fibriquik and MDA® D-dimer latex particle based immunoassay, respectively on plasma collected into 0.105M trisodium citrate (one part plus 9 parts blood) on the MDA 180® (bioMerieux, Inc. Durham, N.C. USA), an automated photo-optical-based coagulation analyser. The DiaMed AG CRP ELISA (Cressier sur Morat, Switzerland) was used and plasma triglyceride (TG) as marker of VLDL was measured using the Sigma Infinity Reagent system. The diagnosis of DIC was performed blinded to the results of the waveform analysis.

APTT Waveform Analysis

Waveform analysis, on the MDA 180® at 580 nm, using Platelin LS reagent on fresh citrated plasma has been well described (for example, Downey, C., Kazmi, R., Toh, C. H. 1997. Novel and diagnostically applicable information from optical waveform analysis of blood coagulation in disseminated intravascular coagulation. *Br. J Haem.* 98:68-73 and Downey, C., Kazmi, R., Toh, C. H. 1998. Early identification and prognostic implications in disseminated intravascular coagulation through transmittance waveform analysis. *Thrombos. Haemostas.* 80:65-69). Quantitation of the degree of biphasic waveform abnormality was by the light transmission level at 18 seconds (TL18) into the APTT reaction with normal waveforms having a mean TL18 of 100% (99.43-100.69) and a mean coefficient of variation of 0.15%.

Materials

Human factors X (FX), V (FV) and prothrombin (FIT) were purified from plasma and converted to FXa and FVa, as previously described. The thrombin chromogenic substrate, S-2238 was obtained from Chromogenix (Milan, Italy). Human recombinant CRP was obtained from Calbiochem (Nottingham, UK) and annexin V from BD Biosciences (San Diego, Calif.) with its flourescein labelled form from Boehringer Mannheim (Werk Penzberg, Germany). Apolipoprotein (apo) B and E standards, Infinity cholesterol/triglyceride reagents, the respective standards and Silica, fumed, were from Sigma (St Louis, Mo.). Goat anti-human apo B-100 and goat anti-human apo E were from Abcam (Cambridge, UK). Rabbit anti-human apo B-100, rabbit anti-human apo E and monoclonal mouse anti-human glycoprotein IB were from Dako (Glostrup, Denmark). Mouse anti-($\alpha_v\alpha_3$) integrin complex and mouse anti-IgG$_1$/G$_{2a}$ were from BD Pharmingen (San Diego, Calif.). Goat-anti-rabbit IgG conjugated to HRP was from Santa Cruz Biotechnology (California, US). Protein G sepharose was from Zymed laboratories Inc. (San Francisco, Calif.). Phospholipid standards were acquired from Sigma, St Louis, Mo. All other regents were of analytical grade.

Chromatography Studies

Size exclusion chromatography was undertaken with a HiPrep Sephacryl S-300 (Amersham Pharmacia, Amersham, UK) column (180 cm$^3$) equilibrated with tris-buffered saline (TBS) pH 8, 2.2 mM CaCl$_2$ at room temperature (RT). 5 ml test serum was applied to the column and fractions were collected every 2 minutes for 90 min at a peristaltic pump speed of 1.5 ml/min. The column was washed with approximately 500 ml 0.2 M sodium hydroxide between runs. The different sera tested were from 2 normal individuals without the biphasic waveform (CRP=5 and 8 μg/ml respectively), 3 ITU patients without the biphasic waveform (CRP=125, 150 and 150 μg/ml) and 4 ITU patients with the biphasic waveform (CRP=120, 130, 145, and 165 μg/ml). In 2 from the last group, the same serum underwent repeat chromatography but in the presence of 10 mM EDTA to disrupt any divalent cation-dependent complex. Fractions were kept at 4° C. and quantified for CRP, apos B and E by ELISA. For apo B/E determinations, 96-well plates were coated overnight at 4° C. with 100 μl goat-anti-human apo B/E at 5 μg/ml in 50 mM sodium hydrogen carbonate pH 9.5, per well. Following washes with 2% BSA/HEPES buffered saline (HBS)/Tween 20, plates were blocked for 1 h at RT with PBS-2% BSA. 100 μl standard (A4183 for apo B and A2673-A2456 for apo E)/sample fractions were applied and incubated for 2 h at RT. Detection was with 100 μl rabbit-α-human apo B/E at 2 μg/ml followed by 100 μl goat-anti-rabbit-HRP conjugate at 1:20000 in washing buffer. The signal was generated with 100 μl 2.9% O-phenylenediamine dihydrochloride in 6 ml deionised water with 2.5 μl 30% hydrogen peroxide (Sigma-Aldrich Company Ltd., St. Louis, Mo., US) and the reaction stopped by 50 μl 0.5M Sulphuric acid. Plates were read on Spectramax Plus (Molecular Devices Corp., Stanford, Calif.) at 490 nm.

Two-dimensional thin layer chromatography (TLC) was performed by the method of Vitiello and Zanetta (Vitiello, F., Zanetta, J. P. 1978. Thin-layer chromatography of phospholipids. *J. Chromatogr.* 166:637-40). In brief, TLC plates (Whatman LabSales, Hillsboro, Oreg.) were activated for 30 min at 125° C. The sample was spotted 15 mm from the edge of the plate and run for 140 mm in methyl acetate: n-propanol: chloroform: methanol: 0.25% potassium chloride (25:25:25:10:9) using a well-saturated tank. The plate was then dried under nitrogen before running in the perpendicular direction in chloroform: methanol: acetone: acetic acid: water (75:15:30:15:7.5), using the same saturation conditions. The plates were then sprayed with ninhydrin (95 ml 0.2% ninhydrin in methanol plus 5 ml 10% aqueous acetic acid) then with 50% aqueous sulphuric acid before heating to 120° C. for 15 min. Standards used were phosphatidylcholine (PC), -serine (PS), -ethanolamine (PE), sphingomyelin (SM), and cerebrosides.

VLDL Isolation and Quantitation

This was as previously described after removal of chylomicrons through centrifugation of test plasma at 14000 rpm for 10 min at 10° C. (1). The VLDL fraction (density<1.019 g/mL) was stored at 4° C. and used fresh within 4 days of isolation.

Prothrombinase Supporting Activity

Isolated VLDL (100, 300, and 500 μM TG) or PC/PS vesicles (75:25) at 50 μmol/L/phosphate, prepared as previously described, were first diluted in TBS (pH 7.4), 5 mmol/L CaCl$_2$ and incubated with 15 nM FVa, 1 μM II. The reaction was initiated with the addition of 0.1 nmol/L FXa. At timed intervals, 10 μl aliquots were taken into 90 μl TBS, 2 mmol/L EDTA. 10 μl was then aliquoted into a 96 well plate, to which 190 μl (400 μmol/L final conc.) of S-2238 was added. Chromogenic liberation at 405 nm was determined on the Spectramax plate reader. Rates of thrombin generation were established by comparison to a calibration curve constructed from a known human thrombin standard. In experiments assessing the contribution of CRP to prothrombinase assembly, 500 μM TG VLDL was incubated with 100 μg/ml CRP for 15 min at RT prior to the introduction of the coagulation proteins into the reaction.

The oxidation status of VLDL was investigated by the method based on thiobarbituric acid reacting substances (Wallin, B., Rosengren, B., Shertzer, H. G., Camejo, G. 1993. Lipoprotein oxidation and measurement of thiobarbituric acid reacting substances formation in a single microtiter plate: its use for evaluation of antioxidants. *Anal. Biochem.* 208:10-5). 75 µl 1.3% thiobarbituric acid (in 0.3% NaOH), 50 µl trichloroacetic acid, 40 µl TBS buffer and 25 µl of VLDL was incubated at 60° C. for 40 min and then cooled on ice. 10 µl 20% SDS was then added prior to absorbance monitoring at A530-A600 nm on the Spectramax reader.

To delineate the contribution of phospholipid surfaces, FACS was performed with flourescein labelled annexin V incubated with VLDL (final concentration 500 µM TG) suspended in HEPES binding buffer, 50 mM calcium on a Becton Dickinson flow cytometer using Cellquest software. The effect of annexin V addition on prothrombinase generation was assessed by prior incubation of increasing annexin V concentrations (0-100 µg/ml at RT for 15 min) with 300 µM TG VLDL in TBS/5 mM $CaCl_2$. In separate experiments, prothrombinase activity was compared after 500 µmol/l TG VLDL in TBS/5 mM $CaCl_2$ was pre-incubated with increasing concentrations (0, 10, 100, 1000 ng/ml) of either annexin V or the phospholipid specific antibody 9D2 (S Ran, University of Texas) at RT for 15 min.

The possibility of platelet or endothelial microparticle contamination in the isolated VLDL was determined by FACS using established platelet and microparticle gates. VLDL (final concentration of 500 µM TG) was incubated with 100 µg/ml flourescein-conjugated monoclonal antibodies specific for platelet glycoprotein 1b and endothelial cell-$\alpha_v\beta_3$ integrin complex (10 µl). The respective isotype controls were used concurrently. Assessment for bound coagulation proteins in the VLDL was by using specific reaction mixes deficient in factors Va, II or Xa for the standard chromogenic prothrombinase assays. The absence of thrombin generation indicated deficiency of the coagulation factor assessed.

Immunoadsorption Analysis

Rabbit anti-human apo B/E (1 mg) were coupled to 150 µl protein G sepharose beads. Control sepharose, without antibody addition, was prepared similarly. 250 µl VLDL standardised for TG was mixed by end over end rotation and incubated overnight at 4° C. Harvested supernatant was analysed for prothrombinase-supporting assembly and apoB/E quantitation, as described above, and by Western blotting. The latter was by way of SDS-PAGE using a 4% stacking gel, and a 5% or 15% running gel for apoe and apoB respectively. 25 µl VLDL in double strength sample buffer was loaded and run at 45 mA for approximately 1 h. Transfer onto Immobilon membrane (Millipore, Billerica, Mass.) was at 400 mA for 1 h and overnight blocking in 5% milk-TBS-0.1% Tween. Incubation was initially with 1 mg/ml antibody apoB/E in 3% milk TBS-0.1% Tween for 1 h at RT and then with anti-rabbit HRP (1 in 6000) in 3% milk TBS-0.1% Tween for 40 min at RT after in-between washing. Following further washing in TBS-0.1% Tween, detection was with chemiluminescence (ECL, Amersham Pharmacia, Amersham, UK) and exposure to x-ray film.

Procoagulant Cofactor Clotting Assay

To determine procoagulant activity of VLDL in the plasma milieu, a modified APTT was performed on the Spectramax microtitre plate reader. 25 µl platelet-poor plasma from normal, overnight-fasted individuals was incubated with 25 µl of 0.175% silica in imidazole buffer at 37° C. After 180 seconds, 50 µl of a 50:50 mix between VLDL (from normal individuals or patients with biphasic waveform abnormalities with equivalent TG levels) and 25 mM $CaCl_2$ was added and the time to clot formation was recorded. This was defined as the time at half-maximum absorbance change. Each run, with all samples performed in duplicates, compared VLDL from a normal versus VLDL from a patient with a biphasic waveform added to the same normal plasma.

Statistics

In the clinical study, non-linear regression analysis with a three-parameter logistic model was fitted to the data in the association between the most abnormal waveform result, the corresponding CRP and TG levels respectively and the diagnosis of DIC (Toh, C. H., Ticknor, L. O., Downey, C., Giles, A. R., Paton, R., Wenstone, R. 2003. Early identification of sepsis and mortality risks through simple, rapid clot-waveform analysis. *Intensive Care Med.* 29:55-61 and Ratkowsky, D. A. 1983. *Nonlinear Regression Modeling*. Marcel Dekker Inc., New York). All these calculations were done using S-PLUS 2000 (MathSoft, Seattle, Wash.). The results from the experimental work were calculated as means +/− SEM. The means were compared using either a univariate ANOVA (prothrombinase) or the analysis of variance by students t-test. Non-parametric testing was also used to supplement the t-test to make no assumption about data distribution. Calculations were performed with the use of SPSS software. A value of $p<0.05$ was used to define statistical significance.

Results

Extent of Correlation to DIC

Figure 4A:
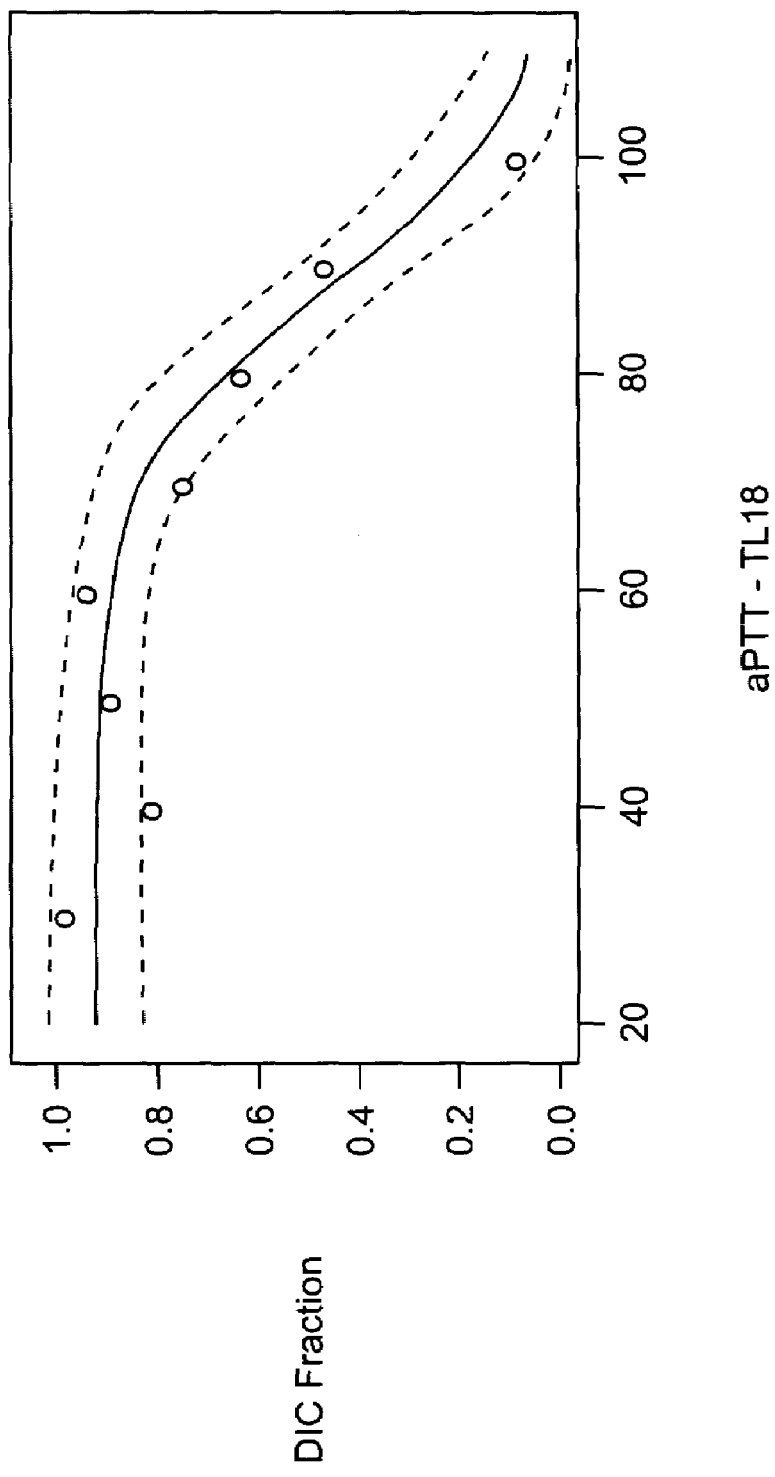
FIGS. 4A-C illustrate logistic models for DIC prediction from (A) APTT-TL18 values, (B) CRP and (C) triglyceride measurements. Open circles are observed fractions; dashed lines indicate 95% confidence limit.
Figure 4B:
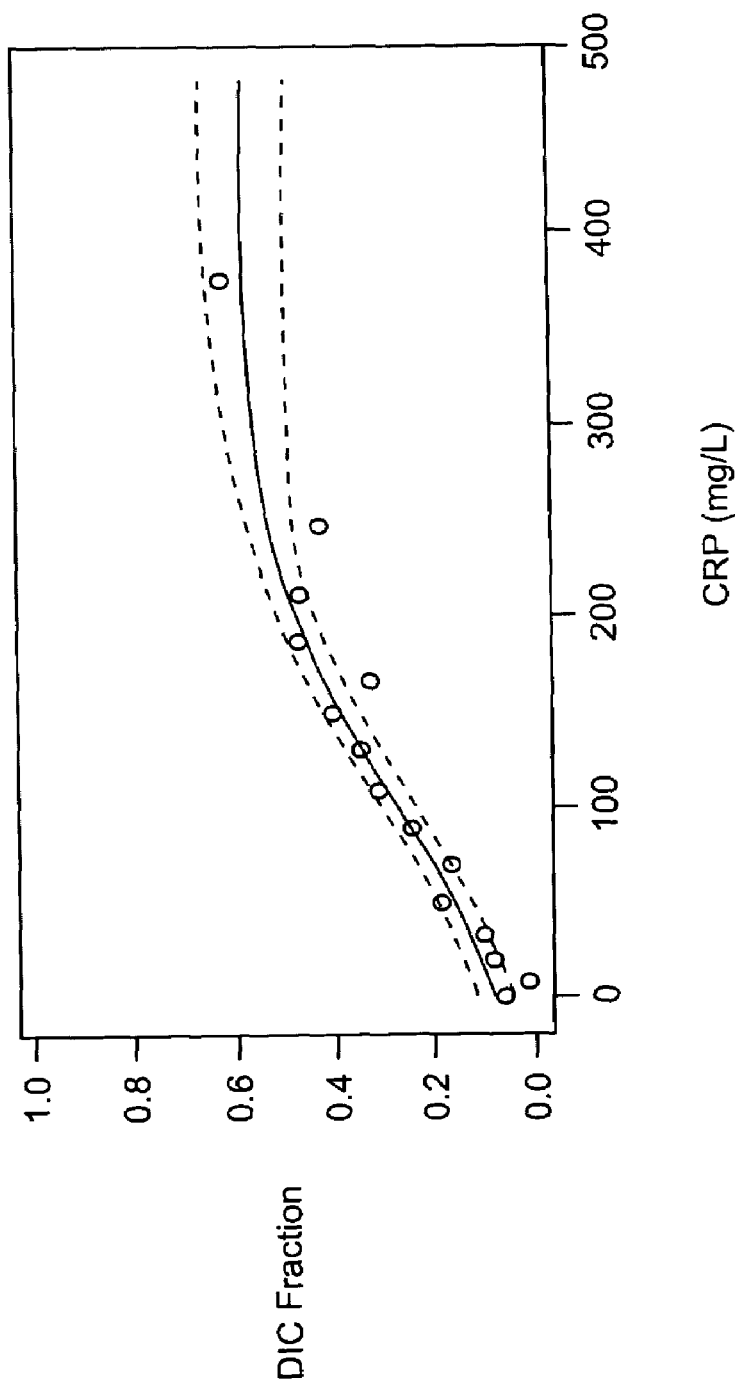
Figure 4C:
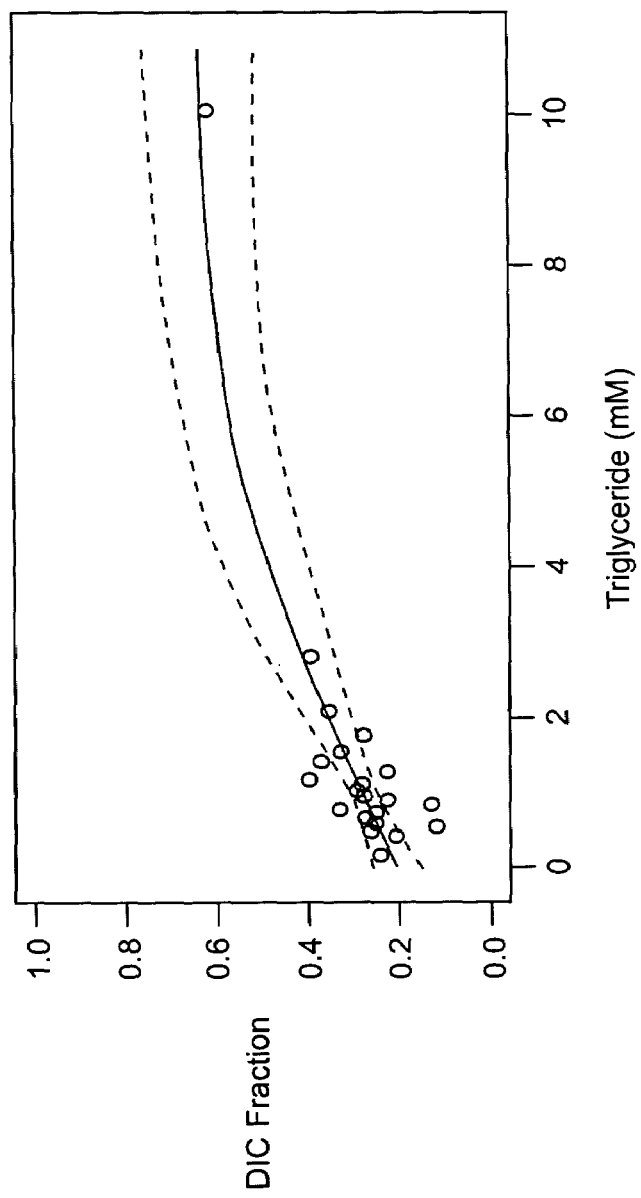

Of a total of 1187 patients admitted consecutively to the ITU over the study period of 24 months, 758 (64%) had a biphasic waveform; i.e. a TL18<99% at some time during the course of their intensive care stay. The data shown in FIG. 4A demonstrates the increasing association between the degrees of waveform abnormality, in reflecting the extent of CRP-VLDL formation, with the diagnosis of DIC. In those with normal waveforms, 10-15% fulfilled the criterion for DIC and this likelihood increased to 60% when the TL18 was reduced by 20%. In those patients with TL18 values of 60% or less, a plateau was reached in the virtual 100% association with DIC. In comparison, the individual components to the complex underlying the biphasic waveform were less strongly associated with DIC as shown in FIGS. 4B and C respectively. The highest levels of CRP and triglyceride, as a marker of VLDL, were associated with DIC in approximately 60% and 70% of cases respectively. Although there were several relatively large triglyceride readings that were highly influential in fitting the logistic curve, as compared to the majority of values, these are shown to reflect the trend of increasing DIC at these large values. These results link high levels of CRP-VLDL complex formation with certainty as to the presence of clinical DIC and that this is as a function of the complex and/or each of its individual components.

Chromatographic Evidence of LCCRP in vivo

Figure 5A:
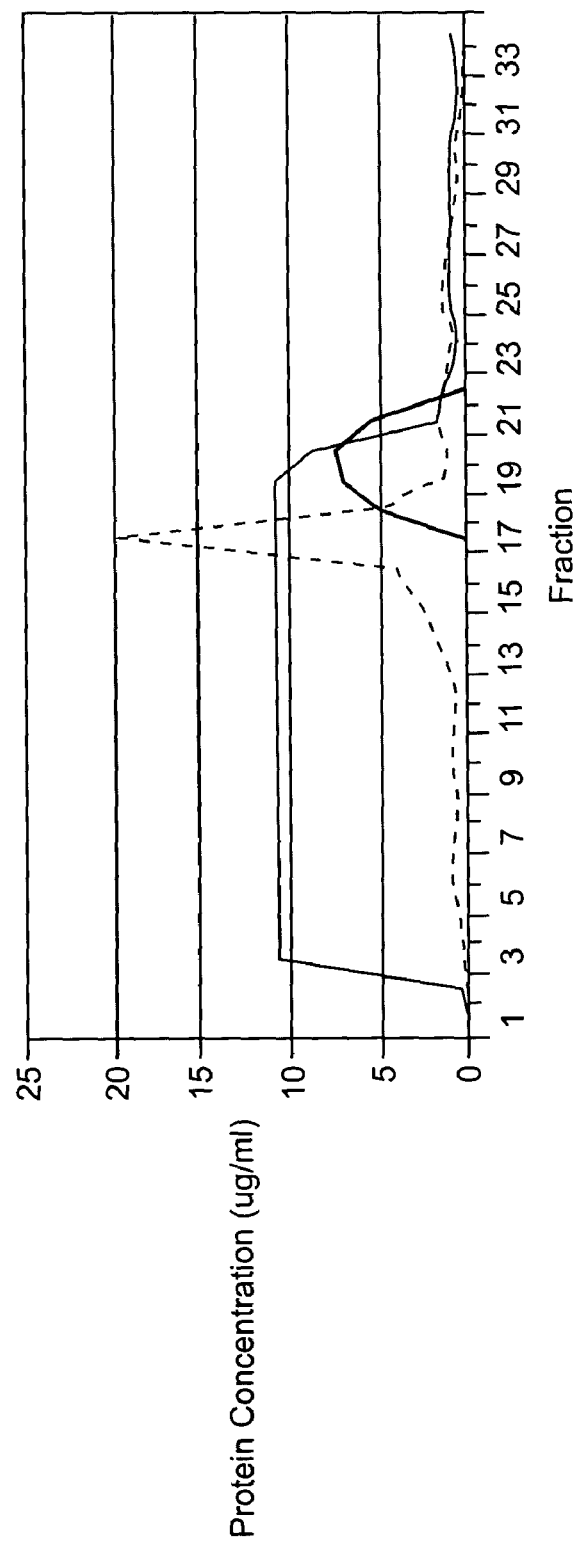
FIGS. 5A-C illustrate size-exclusion chromatography of serum from (A) normal individual, (B) intensive care patient without a biphasic waveform, and (C) intensive care patient with a biphasic waveform. Fractions were measured for CRP (thick line), apo B (thin line) and apo E (dotted line).
Figure 5B:
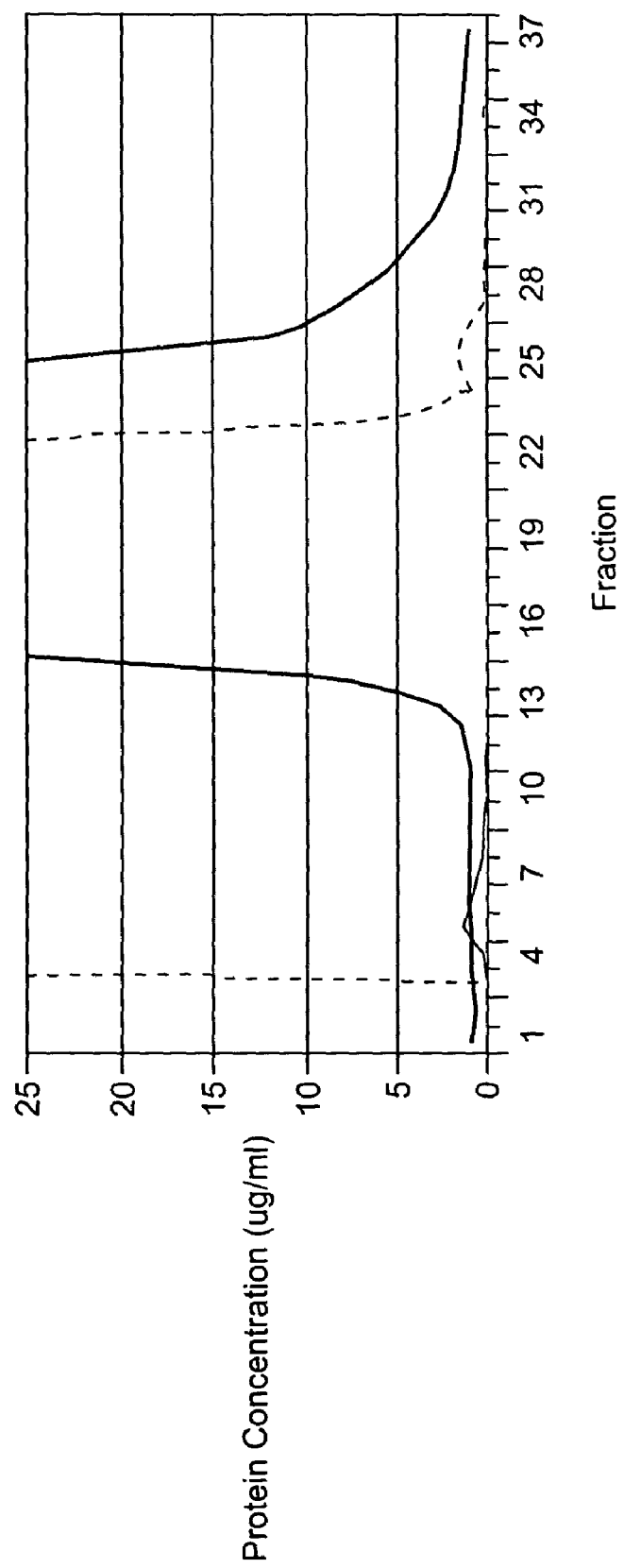
Figure 5C:
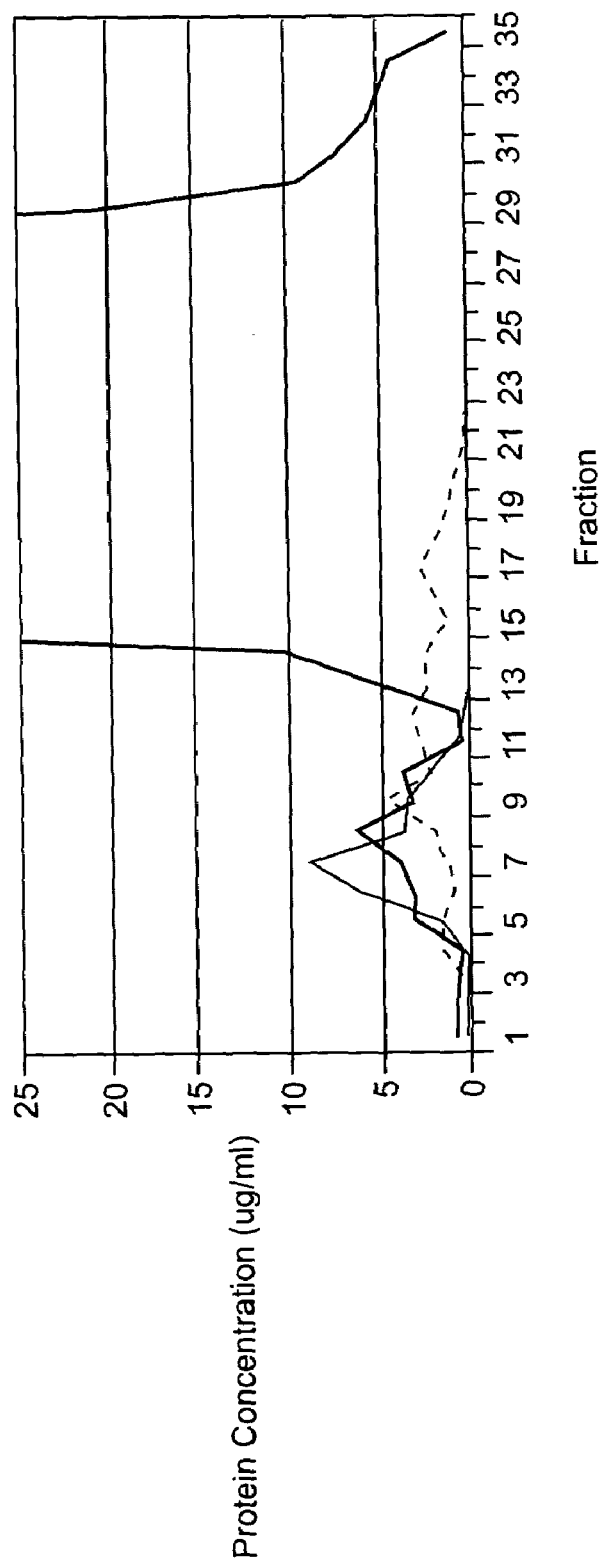

FIG. 5A shows the chromatographic profile from serum of a normal, fasted individual with apo B broadly eluting over early fractions, as a result of its presence in most classes of lipoproteins. Apo E, a marker of the less dense lipoproteins, would generally be detected later on although there would be individual variation. A consistent finding however would be the appearance of CRP as a single peak towards the middle of the elution profile that is greatly amplified, as part of the acute phase response, in intensive care patients. In patients without the biphasic waveform (FIG. 5B), this remains a single peak but a second, smaller and earlier CRP peak would also be detected in patients with the biphasic waveform, which co elutes with apoB and E (FIG. 5C). This earlier CRP peak in a "heavy" form within the void volume also contains peak concentrations of apoB. Its profile is calcium dependent and disappears in the presence of EDTA into the volume of the single CRP peak.

Qualitative and Quantitative VLDL Changes in Patients with the Biphasic Waveform Enhance Prothrombinase Activity.

Figure 6A:
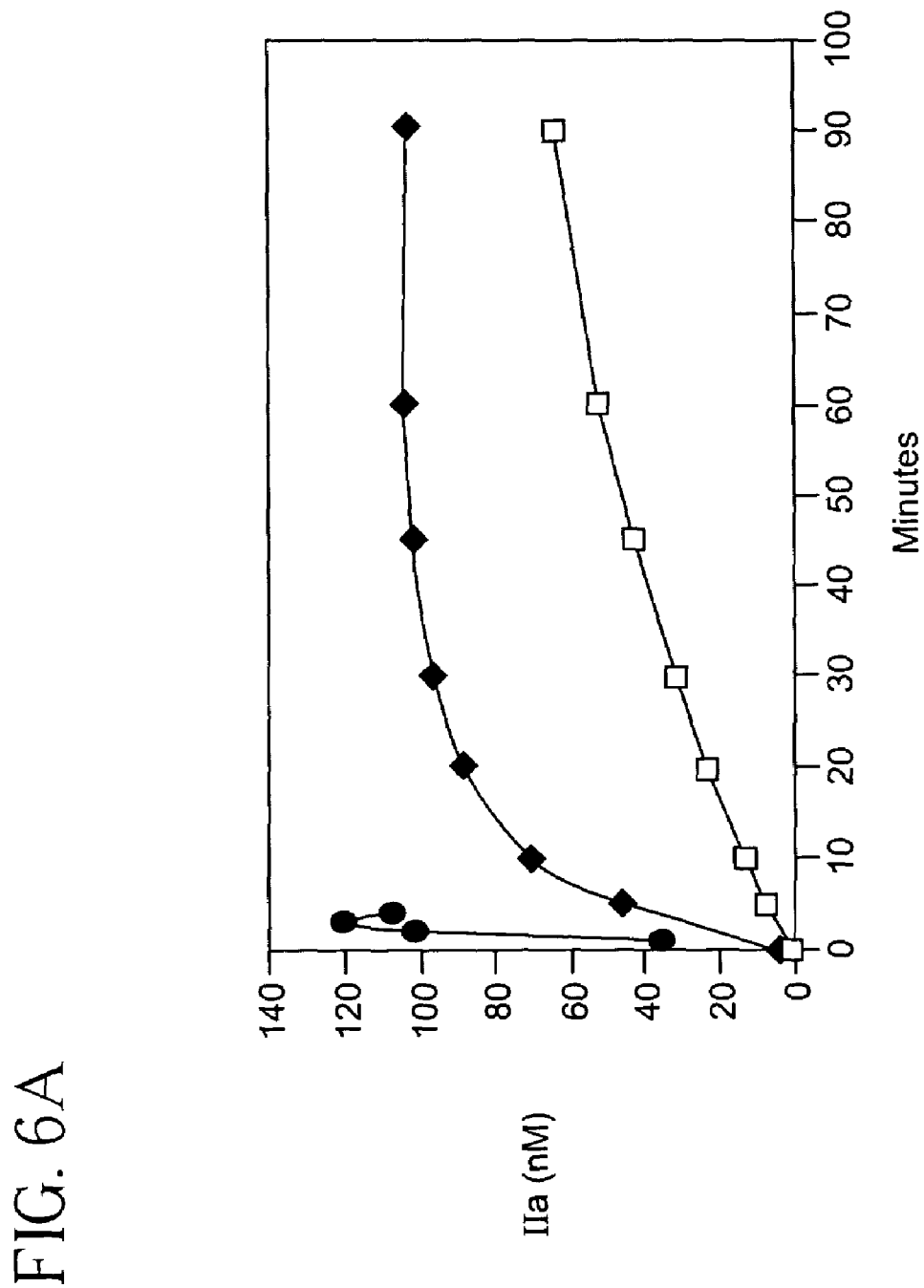
FIGS. 6A-B illustrate prothrombinase supporting activity. (A) shows the comparative activity generated by PCPS (●), VLDL from normal individuals (□) and from patients with the biphasic waveform (♦). (B) shows the differences in 81 samples from normal VLDL (□), intensive care patients with (♦) and without (Δ) the biphasic waveform.
Figure 6B:
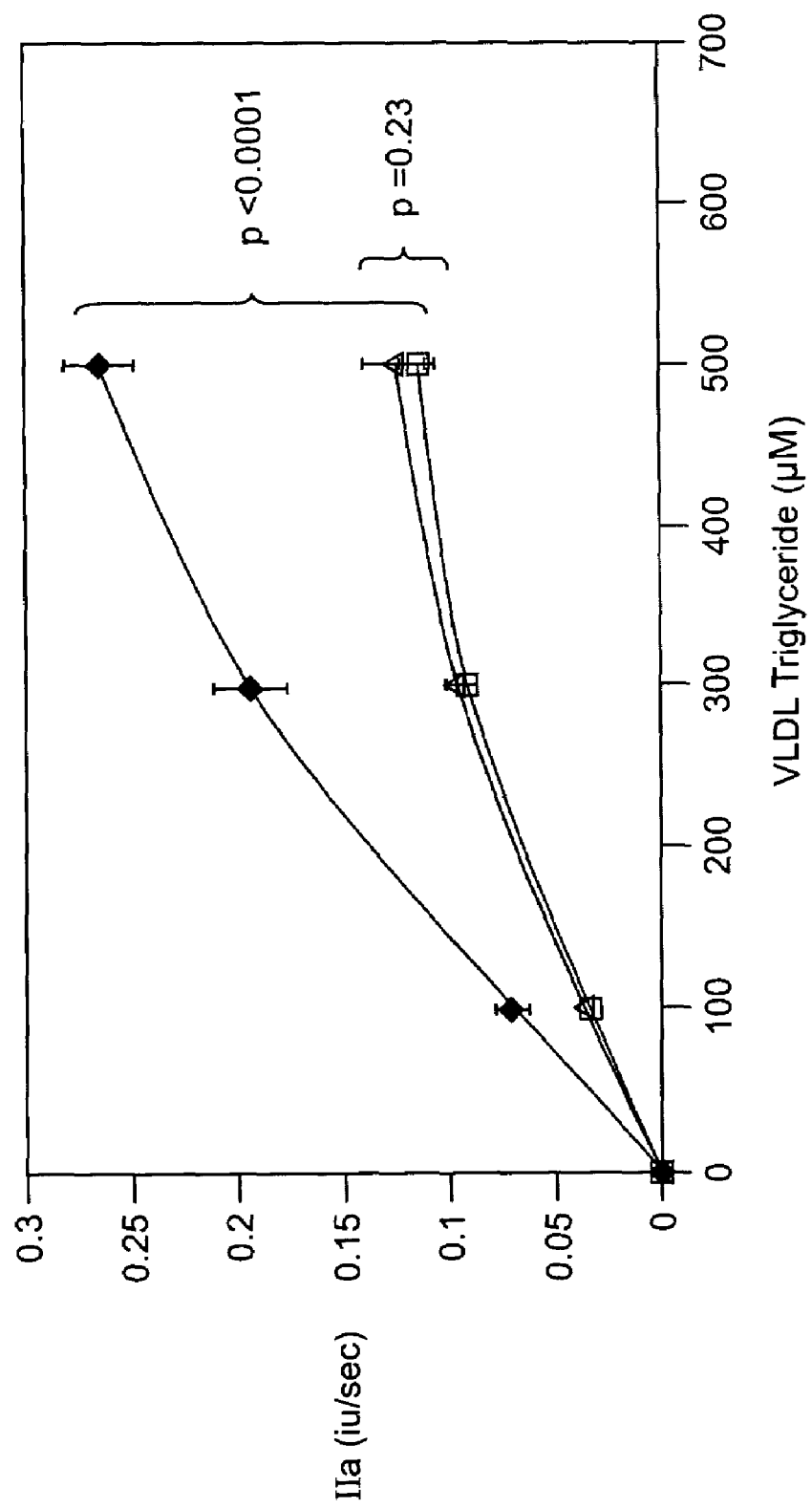

The kinetic contribution of VLDL to thrombin generation was compared to PCPS vesicles. FIG. 6A demonstrates the immediate response with PCPS vesicles with half maximal response within 30 seconds. By comparison, the half maximal response for biphasic VLDL is 8 min and 25 min for normal VLDL. This demonstration of variation in the ability to support thrombin generation was further assessed in a large sample set that also looked at differences between VLDL in different patient groups. Rates of thrombin formation were determined at numerous concentrations of normal VLDL (n=24) and VLDL from ICU patients with (n=25) and without the biphasic waveform (n=22). Slopes of the relationships depicted in FIG. 6B indicate that the biphasic waveform patients were 2.5 fold more potent than normal VLDL and VLDL from ITU patients without the waveform abnormality (p<0.0001). There was no difference between VLDL from normal and patients without the biphasic waveform in the rate of thrombin generation (p=0.23). The inclusion of increasing concentrations of CRP did not significantly vary the rates of thrombin generation from the different groups of VLDL tested.

Figure 7A:
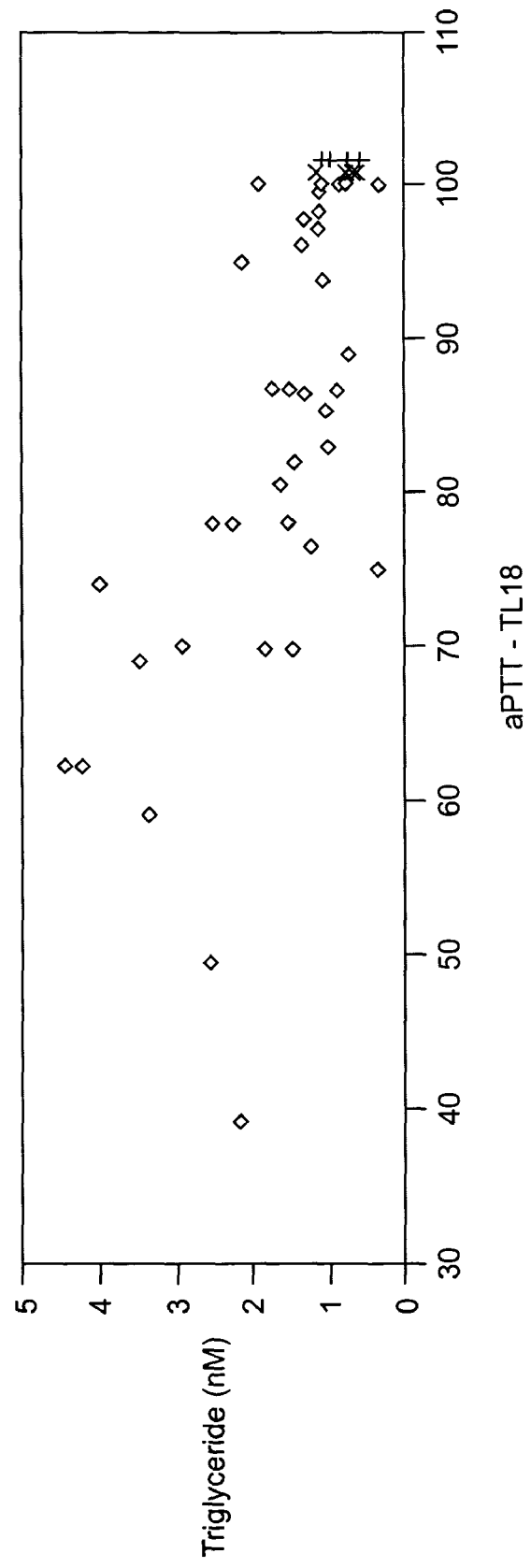

In the same samples, the total triglyceride content had been quantified prior to VLDL separation. FIG. 7A shows that the total triglyceride level is frequently elevated in patients with the biphasic waveform only and there is a positive correlative trend with increasing waveform abnormality. As both qualitative and quantitative changes in VLDL are relevant in terms of thrombin generating potential, the product of total plasma triglyceride and the specific prothrombinase activity [IIa (sec-1)/mM TG] was ascertained. This relationship is demonstrated in individual patient series from samples over several days in FIGS. 7B and C, which respectively illustrate examples of severe sepsis treated to resolution and where there is terminal decline.

VLDL Surface Enhancement of Thrombin Generation in Patients with the Biphasic Waveform Patients.

As phospholipid surfaces are integral to coagulation reactions, we assessed if increased availability on VLDL surfaces could account for the enhanced prothrombinase activity. Utilising fluorescent-labelled annexin V, a calcium-dependent binding protein specific for coagulant-active phospholipids (Meers, P., Mealy, T. 1993. Calcium-dependent annexin V binding to phospholipids: stoichiometry, specificity, and the role of negative charge. *Biochemistry*. 32:11711-21 and Tait, J. F., Gibson, D. 1992. Phospholipid binding of annexin V: effects of calcium and membrane phosphatidylserine content. *Arch. Biochem. Biophys*. 298: 187-91), we compared VLDL from 16 patients with the biphasic waveform to a corresponding number from normal individuals by FACs. The more intense signal from VLDL isolated from the biphasic patients (geo. mean fl 58.02 vs. 19.25) suggests increased coagulant-active lipid exposure. FIG. 8A illustrates typical experimental findings. This was unaffected by incubation with CRP (data not shown). The ability of annexin V to inhibit prothrombinase activity is demonstrated in FIG. 8B with data of VLDL from 4 normals and 4 patients with biphasic waveforms. There was significant inhibition of thrombin generation for biphasic VLDL at 100 ng/ml annexin V (p=0.003). The degree of inhibition of prothrombinase activity is far greater on the VLDL derived from patients with the CRP-VLDL complex when compared to normal thereby suggesting that the increased thrombin generation was due to increased coagulant-active phospholipid exposure in VLDL from biphasic waveform patients.

This enhanced procoagulant potential could be explained by either in vivo and/or ex vivo contamination with platelet or endothelial microparticles. This was excluded as flow cytometry of lipoprotein microparticles failed to identify fragments specific for endothelial cells and platelets. In addition, the possible contribution of bound prothrombinase proteins to the harvested VLDL was also investigated. No significant thrombin was generated in the absence of purified factors Va, II or Xa by means of the prothrombinase assay, indicating absence of relevant coagulation protein association with the VLDL.

To assess if this increased coagulant activity was due to increased PS exposure in VLDL from patients with the biphasic waveform, the 9D2 monoclonal antibody (Dr Ran, Univ. of Texas) was used in 3 separate experiments. This has well characterised specificity for PS, phosphatidic acid, cardiolipin, phosphatidyl-inositol and -glycerol with no reactivity to PC, PE and SM (Ran, S., Downes, A., Thorpe, P. E. 2002. Increased exposure of anionic phospholipids on the surface of tumor blood vessels. *Cancer Res*. 62:6132-6140). FIG. 8B shows that it has no significant inhibitory effect on the surface ability of VLDL to support prothrombinase activity. This suggests that changes in PS are not responsible for the prothrombinase enhancement.

VLDL from Biphasic Waveform Patients Lack PE but Similarly Contain PC, SM and Cerebrosides.

Figure 9B:
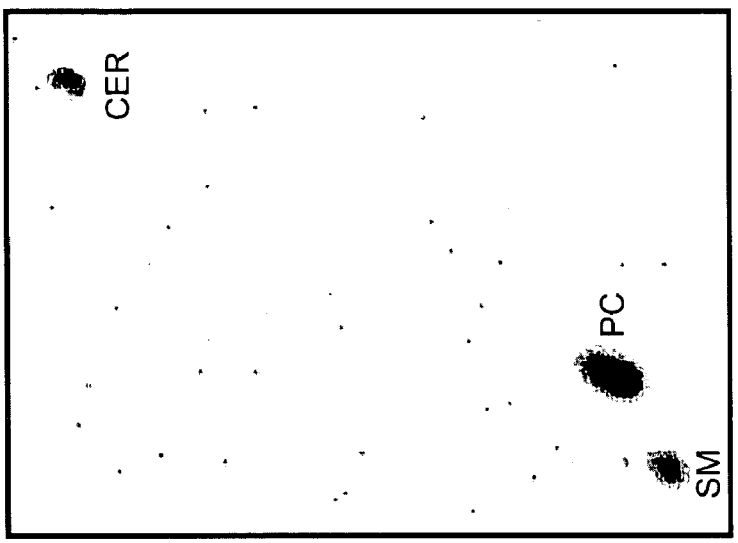
FIGS. 9A-B illustrate two dimensional thin layer chromatography comparison of (A) normal and (B) biphasic waveform patient VLDL with PC denoting phosphatidylcholine; PE, phosphatidylethanolamine; SM, sphingomyelin; Cer, cerebrosides.
Figure 9A:
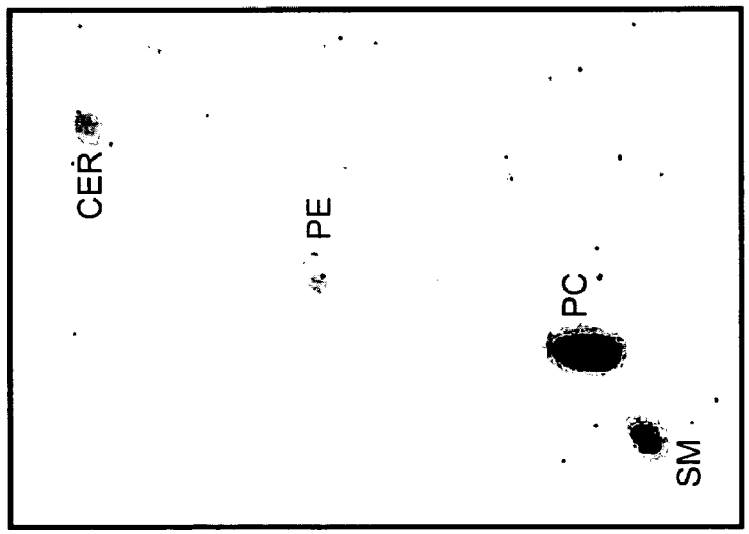

To validate the above findings and further investigate the phospholipid moieties involved, TLC was performed. The method, in being sensitive down to detection limits of 0.25 µg of amino-containing phospholipid, confirmed the lack of PS in VLDL from both normal individuals (n=5) and patients (n=10). PC, SM and cerebrosides were present in all VLDL, thus explaining the relative lack of 9D2 antibody abrogation of thrombin generation (FIG. 9A). The only compositional difference was a lack of PE in biphasic waveform patients only (FIG. 9B). This was a reproducible finding that was specific for patients with the biphasic waveform as ICU patients without the waveform abnormality had TLC findings similar to that of normal.

Figure 10:
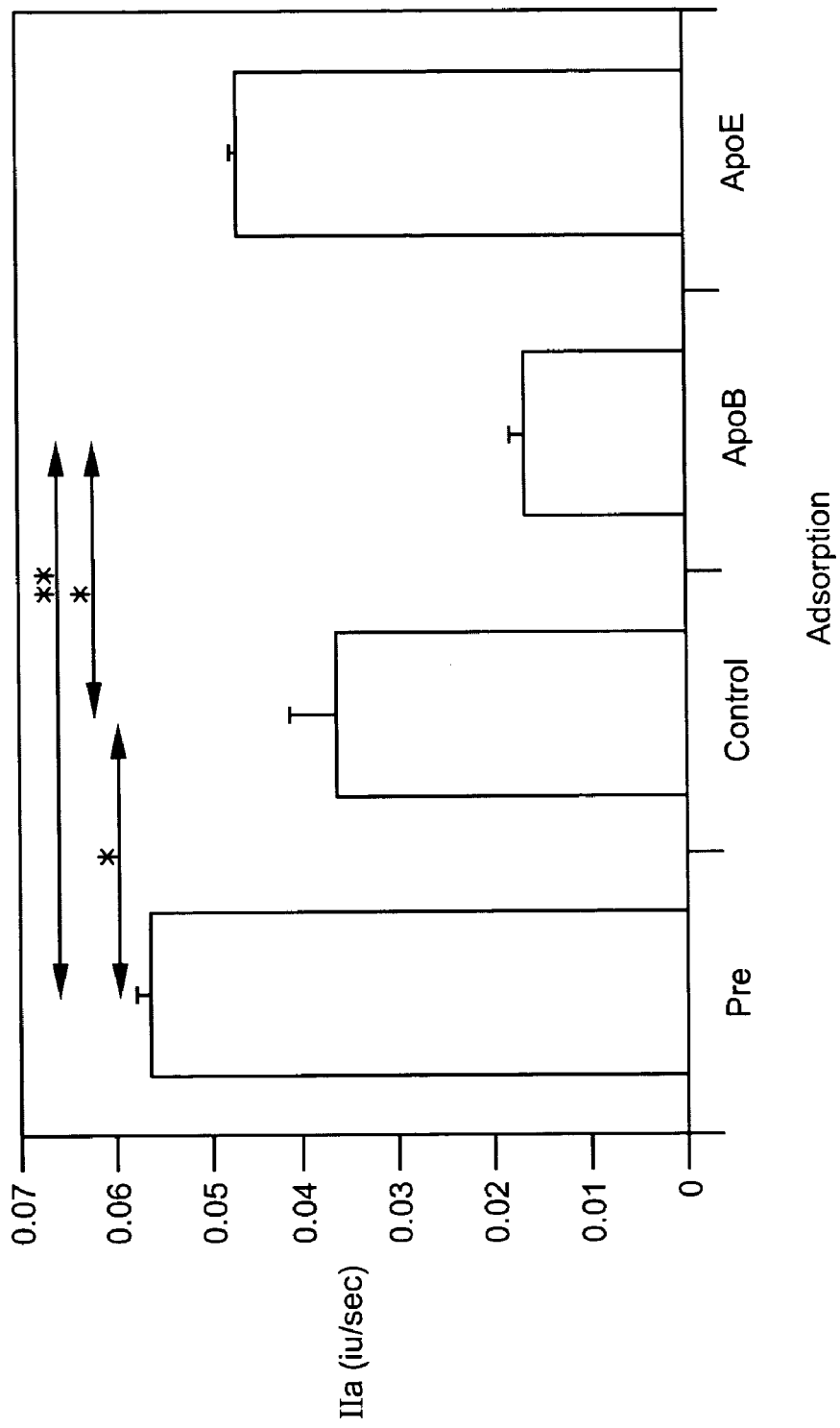
FIG. 10 illustrates prothrombinase activity of VLDL from biphasic waveform patients (n=3) before and after controlled, apo B and apo E immunoadsorption expressed as mean±SEM (* p<0.01, ** p <0.002).
Figure 11:
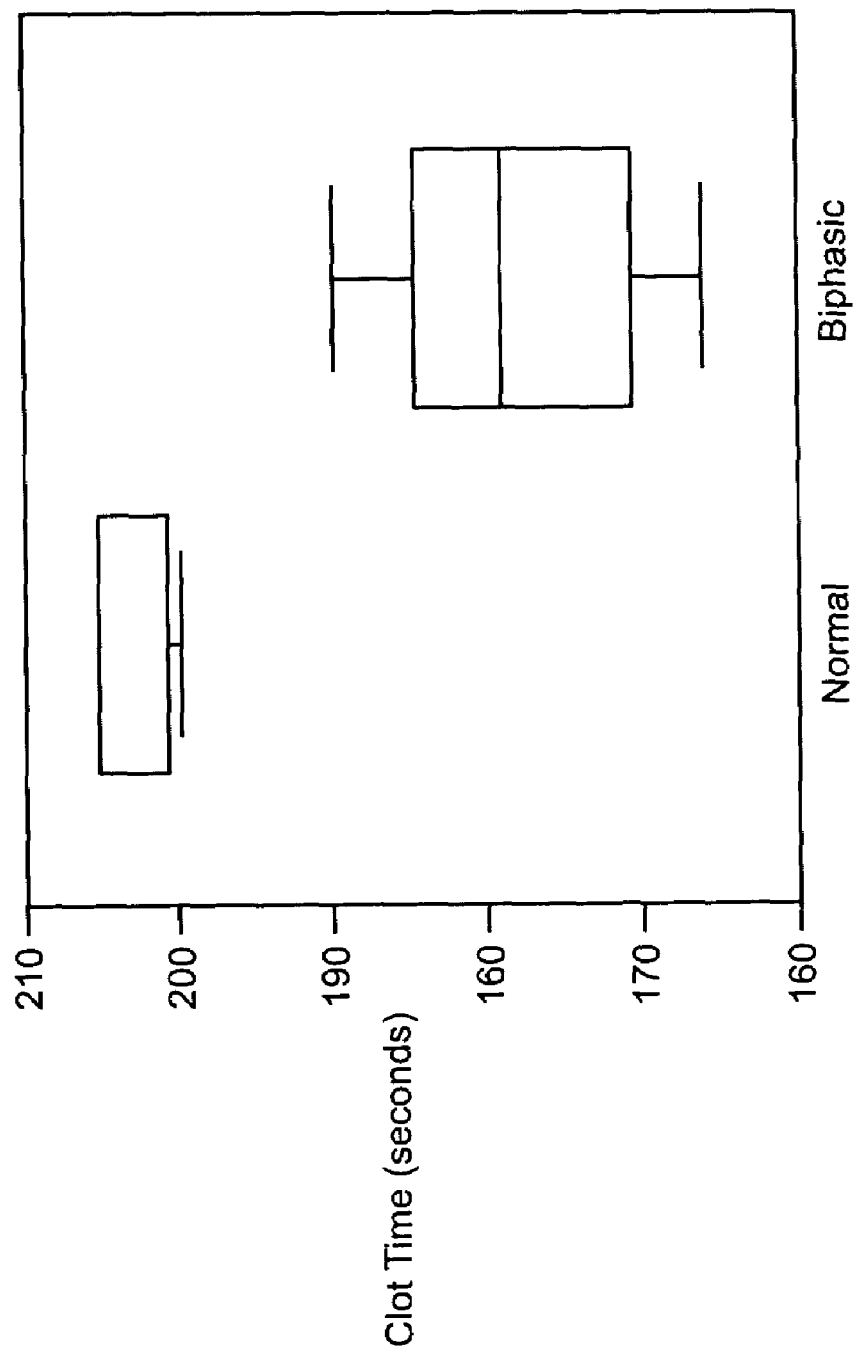
FIG. 11 illustrates comparative procoagulant cofactor activity of VLDL from 7 normal versus 7 patients with biphasic waveforms in a modified APTT clotting assay. The box plot represents the $25^{th}$ to $75^{th}$ percentile interquartile ranges of the clot times (in seconds) generated. The thickened line represents the median and the extreme upper and lower data points are represented outside the interquartile range.

Immunoadsorption of Apolipoprotein B from VLDL Disrupts the Particle Structure and Ability to Support Thrombin Generation To define the contribution of VLDL proteins, immobilised antibodies against apo B-100 or apo-E were tested for their ability to adsorb prothrombinase activity. Anti-apo B IgG adsorbed 80% of the prothrombinase activity when compared with control sepharose beads. Based on SDS-PAGE and densitometric analyses, immobilised anti-apoB antibody adsorbed the target antigen; i.e. the stained apo B protein band in adsorbed supernatant was 5% of that from control Sepharose beads. The adsorption process itself leads to loss of prothrombinase potential but specific apo B removal leads to significant loss of activity (p=0.0002) in 3 different starting VLDL (FIG. 10). Further flow cytometric analysis to assess VLDL structural integrity after apo B immunoadsorption showed no identifiable particles. This suggests that apo B contributes to the enhanced thrombin generation of VLDL from biphasic waveform patients by structurally supporting the necessary conformation of lipids to enhance prothrombinase assembly.

By contrast, immunoadsorption of apo E down to levels less than 5% compared with controlled adsorption did not diminish prothrombinase activity (FIG. 10) or its structural integrity by FACs. Apo E is therefore not essential in the surface configuration that optimises thrombin enhancement.

VLDL from Biphasic Waveform Patients Show Procoagulant Activity in Clotting Assays of Normal Plasma Following on from the above prothrombinase findings, we examined for procoagulant cofactor activity of VLDL in the plasma milieu using a modified APTT clotting assay. As seen in FIG. 10, the addition into normal plasma of isolated VLDL from biphasic waveform patients showed significant shortening of clot time when compared with addition into the same plasma of equivolume VLDL from normal individuals (p=0.000). The mean clot time was 203 seconds (SEM 0.95) for VLDL from 7 normal unrelated donors and this decreased to 178 seconds (SEM 3.02) for VLDL from 7 patients with biphasic waveforms (TL18 77-85). The box plot in FIG. 10 shows the interquartile ranges from $25^{th}$ to $75^{th}$ percentile and median clot times of 205 and 179 seconds respectively for normal or biphasic VLDL addition. This clear difference could not be accounted for by differences in total TG content with considerable overlap between normal (range of 0.4 to 1.5 mM) and biphasic waveform patients (range 0.5 to 1.8 mM). Thus, VLDL from patients who exhibit the biphasic waveform show significant procoagulant cofactor activity.

In this study, we were able to demonstrate that VLDL from patients with the biphasic waveform had at least twice the thrombin generating potential of normal VLDL and that this was not due to lipid oxidation or contamination with microparticles. While previous studies have established that normal VLDL can generate physiological levels of thrombin albeit with considerable donor variability (Moyer, M. P., Tracy, R. P., Tracy, P. B., van't Veer, C., Sparks, C. E., Mann, K. G. 1998. Plasma lipoproteins support prothrombinase and other procoagulant enzymatic complexes. *Arterioscler. Thromb. Vasc. Biol.* 18:458-465 and Rota, S., McWilliam, N. A., Baglin, T. P., Byrne, C. D. 1998). Atherogenic lipoproteins support assembly of the prothrombinase complex and thrombin generation: modulation by oxidation and vitamin E. *Blood*. 91:508-15), this differential increase was consistent in patients with the biphasic waveform within the large sample set investigated and could play a significant role supporting thrombin generation in vivo.

Although we initially hypothesised that the increased thrombin generating potential in VLDL from patients with the biphasic waveform, was due to increased anionic phospholipid availability, we were unable to show that this was due to increased phosphotidylserine. This was on the basis of two separate lines of evidence. Firstly, the data from the 9D2 blocking antibody with well-characterised specificity for PS showed no inhibition of prothrombinase activity. Secondly, the TLC studies which would have been sensitive to detecting 0.25 μg of PS showed no evidence even in VLDL from biphasic waveform patients with enhanced prothrombinase supporting activity. Deguchi et al have found a small amount of PS (0.4%) in normal VLDL (Deguchi, H., Fernandez, J. A., Hackeng, T. M., Banka, C. L., Griffin, J. H. 2000 Cardiolipin is a normal component of human plasma lipoproteins. *Proc. Natl. Acad. Sci. USA*. 97:1743-1748) and it may be that trace amounts could support prothrombinase activity (Moyer, M. P., Tracy, R. P., Tracy, P. B., van't Veer, C., Sparks, C. E., Mann, K. G. 1998. Plasma lipoproteins support prothrombinase and other procoagulant enzymatic complexes. *Arterioscler. Thromb. Vasc. Biol.* 18:458-465). However, there could be alternative explanations especially as the most appropriate composition of phospholipids for activating the prothrombin complex in vivo is still a matter of debate. The importance of PS stems from in vitro studies under static conditions where compositional PC:PS ratios of 3:1 appear most similar to the procoagulant effect of activated platelets (Deguchi, H., Fernandez, J. A., Hackeng, T. M., Banka, C. L., Griffin, J. H. 2000 Cardiolipin is a normal component of human plasma lipoproteins. *Proc. Natl. Acad. Sci. USA*. 97:1743-1748). By contrast, vesicles containing PC alone can cause the highest increase in procoagulant activity, as measured by fibrin deposition (Higgins, D. L., Callahan, P. J., Prendergast, F. G., Nesheim, M. E., Mann, K. G. 1985. Lipid mobility in the assembly and expression of the activity of the prothrombinase complex. *J Biol. Chem.* 260:3604-3612). PC may be particularly relevant in interpreting our findings and Rosing et al have also shown the ability of positively charged membranes to enhance prothrombin activation (Galan, A. M., Hernandez, M. R., Bozzo, J., Reverter, J. C., Estelrich, J., Roy, T., Mazzara, R., Ordinas, A., Escolar, G. 1998. Preparations of synthetic phospholipids promote procoagulant activity on damaged vessels: studies under flow conditions. *Transfusion*. 38:1004-1010). The findings that PE was absent specifically from VLDL of patients with the biphasic waveform may also be important especially in the effect of shortening plasma clot times. PE is largely considered to promote anticoagulant pathways and its blockade by antiphospholipid antibodies promotes the procoagulant activity of thrombin (Rosing, J., Speijer, H., Zwaal, R. F. 1988. Prothrombin activation on phospholipid membranes with positive electrostatic potential. *Biochemistry*. 27:8-11). However, in addition to compositional differences, conformation in the presentation of appropriate surfaces for coagulation reactions also needs to be considered. The loss of prothrombinase activity through apoB immunoadsorption in disrupting lipoprotein integrity highlights this particular aspect.

As shown, VLDL from patients manifesting the biphasic waveform can significantly enhance thrombin generation. Moreover, the calculation of total thrombin generating capacity from the quantitative and qualitative changes in VLDL within serial samples of patients with sepsis and DIC show a direct positive correlation with clinical progression. This supports the relevance of thrombin as a major player in the pathophysiology of sepsis. Whilst its primary role may have been as part of the acute phase protective initial response, the protracted or enhanced response fuelled by VLDL procoagulant surfaces may lead to deleterious consequences.

Example 2

Measurements of CRP and VLDL. In fifteen patient plasmas of patients exhibiting a biphasic waveform, VLDL measurements were obtained by initial centrifugation at 356,000×g at 10° C. for 2 h in polycarbonate centrifuge tubes (11×34 mm, Beckman Instruments, Palo Alto, Calif.) in a Beckman TL-100 tabletop ultracentrifuge. The upper VLDL fraction was collected and the volume recorded. LDL, isolated as described Gabel, B. R., et al. *Biochemistry*, 1998,37:7892-7898 and Wang, X. et al. *Arterioscler. Thromb. Vasc. Biol.*, 200, 20:1301-1308, was used as the standard for the ApoB-100 ELISA. The cholesterol concentration was determined calorimetrically at 500 nm in the isolated VLDL fractions from biphasic patient and normal plasma samples using the Cholesterol Infinity Reagent and Cholesterol Calibrator according to the manufacturer's protocol. The total protein concentrations in the recovered VLDL fractions were determined with the Bradford assay using BSA as a standard. CRP levels were determined by ELISA using a rabbit anti-human CRP IgG for capture with detection by the same antibody, conjugated to HRP in the method described by Tijssen, et al. *Analytical Biochemistry*, 1984, 136: 451-457. CRP was also determined in the 1187 clinical study patients with levels cross-checked using the Eurogenetics kit. As a marker of VLDL levels, triglyceride concentrations were also determined in the same cohort.

CRP Detection in Isolated VLDL Fractions from Patient Sera.

Serum from four patients with varying degrees of the BPW was obtained. Each of these was divided into three 0.9 ml aliquots. The first aliquot was left as collected. One-tenth ml of 0.1M EDTA was added to the second aliquot to chelate and disrupt any complex that might be present. One-tenth ml of 0.25M $CaCl_2$ was added to the third aliquot to optimize complex formation. All samples were then centrifuged as described above for VLDL isolation. The isolated fractions were then measured for CRP and triglyceride (Sigma Diagnostics Infinity Reagent) with values then expressed as CRP per mM VLDL triglyceride measured.

Prothrombinase Supporting Activity of Isolated VLDL.

The isolated VLDL of 3 patients with a BPW, along with a sample isolated from a pool of 20 healthy volunteers, were analyzed for their ability to replace the phospholipid component in prothrombin activation. The VLDL concentrations were adjusted to 100, 200 and 300 µM (cholesterol) and initial rates of thrombin formation were measured by fluorescence in a fluorescence microtitre plate reader by a procedure generally described by Nesheim, M. E., et al., *J Biol. Chem*. 1979, 254: 10952-10956.

Evidence for the Existence of the CRP/VLDL Complex in the Sera of Patients with the Biphasic Waveform.

Although the inference could be drawn that CRP/VLDL complex would exist in circulation due to the presence of plasma $Ca^{2+}$, the possibility that the complex might form due to the initial exposure to the anticoagulant used to prepare the plasma samples prior to recalcification was investigated. Experiments were performed in an effort to identify the complex in the sera of blood not exposed to the anticoagulant. CRP was detected by ELISA in VLDL isolated from untreated sera of patients with the BPW as shown in Table I, below.

did not have detectable CRP and patients with high CRP without a BPW had no recoverable VLDL. From these observations, it was concluded that the complex does exist to a measurable extent in the blood of patients whose plasmas exhibit a BPW.

Example 3

Twenty samples from patients experiencing an acute phase response as evidenced by elevated levels of IL-6, CRP, fibrinogen and/or SAA were examined. All twenty patients showed some degree of activated coagulation and displayed marked disruptions in their lipoprotein profile, with all patients experiencing hypolipidemia in the form of low cholesterol and often low triglyceride levels. Sixteen of the 20 patients were adjudicated as having been infected during or prior to ICU admission. The lipoprotein profiles and VLDL properties were studied in the manner described below.

Lipoprotein Profiles

A portion of each plasma was sent for a lipoprotein profile measured by NMR analysis to obtain additional information not found in the classic lipid chemistries currently in common use by clinical laboratories. NMR analysis provided a quantitative analysis of the number of lipoprotein particles at a given size, regardless of the lipid chemistry of the particle. From this analysis, two observations were common for all subjects. The HDL sized particles decreased in quantity by over 50% from normal particle concentrations. VLDL sized particles also decreased in all subjects during the protocol blood work. The drop in VLDL quantities varied depending on the day of blood work.

The quantity of LDL sized particles showed some variation depending on the day of blood work, but was less variable than seen with VLDL and HDL sized particles. Four of the samples displayed very low LDL levels for a period of time during the ICU study.

To get an idea of the overall changes in all lipoprotein classes, a calculation was performed to calculate the total surface area from all of the lipoprotein classes. By performing this calculation, it is an indirect indicator of the amount of total core lipids that the lipoproteins could potentially carry. Six of the 20 subjects showed total drops in lipoprotein levels (via surface area) of greater than 67% with 13/20 showing drops of greater than 50%. This is summarized in Table II below.

TABLE I

CRP in VLDL fractions from Untreated, EDTA and Calcium Treated Samples of Serum from Patients with Positive Biphasic Waveforms

| Patient No. | Serum CRP (µg/ml) | VLDL fraction Total CRP | VLDL fraction CRP mM Trig | VLDL fraction plus EDTA Total CRP | VLDL fraction plus EDTA CRP mM Trig | VLDL fraction plus $Ca^{2+}$ Total CRP | VLDL fraction plus $Ca^{2+}$ CRP mM Trig |
|---|---|---|---|---|---|---|---|
| 1 | 323 | 14.3 | 1.29 | 1.3 | 0.08 | 160 | 21.92 |
| 2 | 281 | 18.6 | 4.04 | 1.1 | 0.15 | 172 | 40.95 |
| 3 | 264 | 4.2 | 1.17 | 0.9 | 0.12 | 157 | 50.70 |
| 4 | 218 | 21.5 | 9.77 | 2.2 | 0.85 | 157 | 112.14 |

As the interaction between CRP and VLDL is $Ca^{2+}$-dependent, prior chelation of the sample led to a loss of detectable CRP in all patients examined. Likewise, prior incubation with additional $Ca^{2+}$ to promote complex formation between CRP and VLDL led to enhanced detection of CRP within the VLDL fraction. VLDL from normal patients

TABLE II

Lipoprotein Surface Area

| Patent Number | Total Lipoprotein Surface Area % Drop from Normal |
|---|---|
| 1 | 58 |
| 2 | 44 |
| 3 | 60 |
| 4 | 68 |
| 5 | 53 |
| 6 | 76 |
| 7 | 53 |
| 8 | 38 |
| 9 | 68 |
| 10 | 55 |
| 11 | 41 |
| 12 | 53 |
| 13 | 38 |
| 14 | 50 |
| 15 | 49 |
| 16 | 79 |

TABLE II-continued

Lipoprotein Surface Area

| Patent Number | Total Lipoprotein Surface Area % Drop from Normal |
|---|---|
| 17 | 70 |
| 18 | 44 |
| 19 | 37 |
| 20 | 74 |

Average nanoMolar Normal Pool Area
9.13 × 10 ^6 nm ^2/L
To calculate surface area:
Average diameter of VLDL = calculated by NMR (Range 33 to 140 nm).
Average diameter of LDL = calculated b NMR (Range 19-22 nm).
Average diameter of HDL = calculated by NMR (8-11 nm).
All lipoprotein concentrations give by NMR and nMolar.
Formula would then be 4 * 3.1416 * (average diamter/2)^2*(lipoprotein concentration in nMolar).

VLDL Properties

The VLDL of the 20 patient samples was isolated for each specimen by ultra centrifugation at the density of 1.006 g/cc (unadjusted density). This buoyant density subclass was then analyzed by agarose electrophoresis side by side with the initial plasma. Isolated from normal sera, the lipoproteins from this buoyant density (termed VLDL) usually showed pre-beta migration patterns upon electrophoresis in non-denaturing agarose gels. A typical pattern emerged upon isolation and fraction, all patients experienced the electrophoretic shift from pre-beta migration to some degree of beta migration. Often there was observed an evidence in the VLDL of the complete shift to beta migration on at least one day of the ICU blood work or upwards to an entire week.

From running the total plasma on the agarose gel, changes in the HDL migration patterns were also noted. In normal donors, HDL migrates at the alpha region. For all ICU patients (twenty), the HDL changed migration to a post-alpha/pre-beta which is indicative of the serum amyloid A (SAA) incorporation.

Figure 12A:
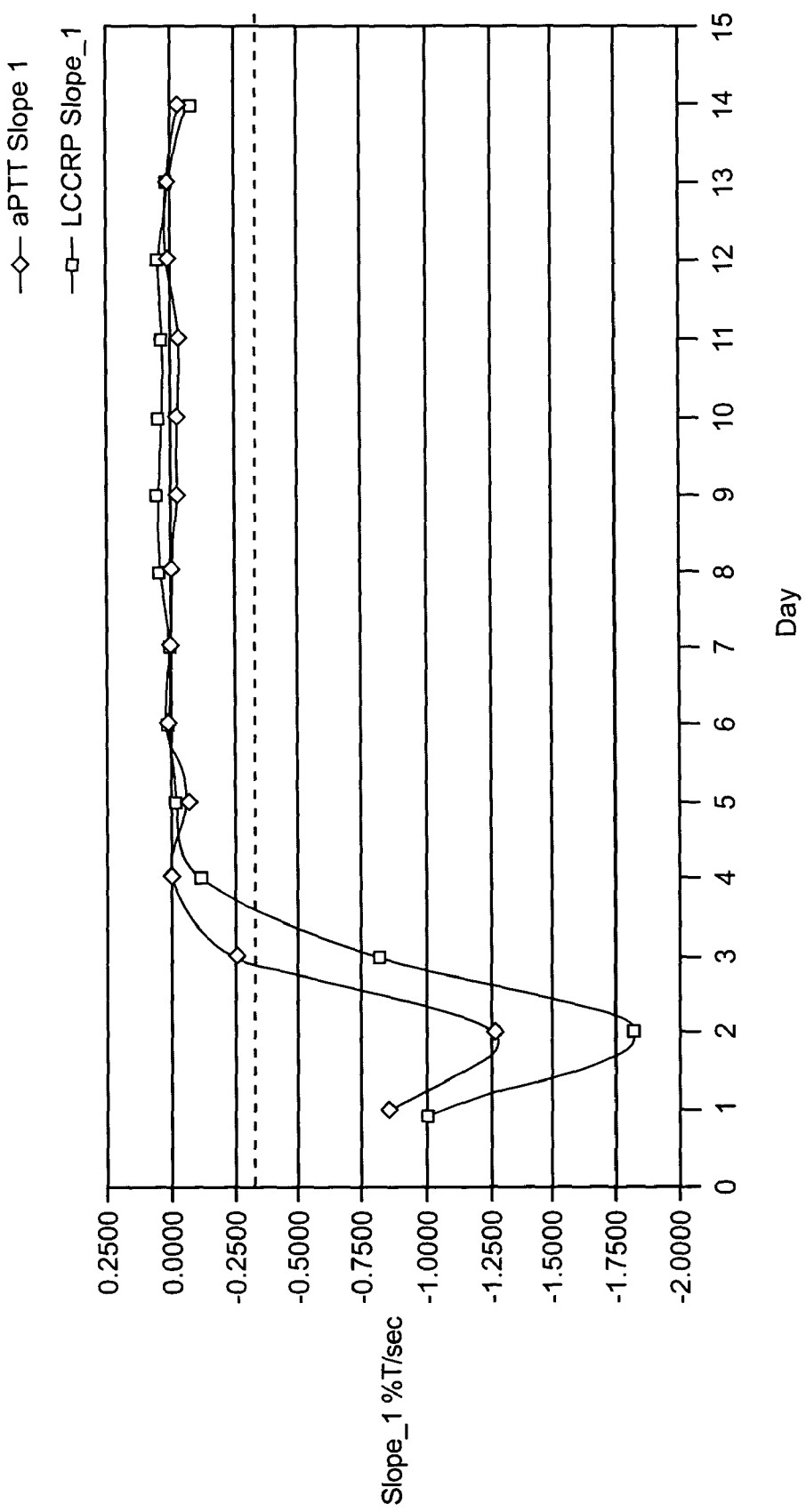

A portion of the isolated VLDL was run on reducing SDS polyacrylamide gels. VLDL is a lipoprotein which usually contains five plus proteins: apo-B, apo-E, apo-Cl, apo-Cll, apo-Clll are the most commonly found proteins in normal VLDL. By SDS-page analysis, there appeared to be changes in the proteins as analyzed within a patient's stay in the ICU. Apo-B was always present. The apo-C's were difficult to analyze due to their small size, but there did appear to be some changes occurring during the patient's stay in ICU. Apo-E changes were the most common and obvious change seen with the 20 ICU patients. At times the apo-E band disappeared during the patient's stay. FIG. 12A shows the serial sample biphasic slope-1 data from a patient identified as Patient 20. FIG. 12B shows the corresponding agarose gels that illustrate a shift in mobility of VLDL for the patient FIG. 12A. The shifts in lipoproteins corresponded with the appearance of the abnormal waveform patterns.

That which is claimed is:

1. A method for diagnosing and monitoring a host response to severe infection, said method comprising (a) obtaining a patient sample; (b) measuring prothrombinase activity of a lipoprotein fraction from said sample; and (c) correlating said measurement of prothrombinase activity of said patient's sample to a condition of severe infection when said measurement shows at least about a two-fold increase in prothrombinase activity compared to a sample of a normal, healthy person.

2. The method according to claim 1, wherein said lipoprotein fraction comprises beta lipoproteins.

3. The method according to claim 2, wherein said step (b) is carried out by measuring rate of thrombin generation and said beta lipoprotein comprises an apoB containing lipoprotein.

4. The method according to claim 2, wherein said step (b) is carried out in the absence of forming a complex between said betalipoprotein and C-reactive protein (CRP).

5. A method according to claim 1 wherein said severe infection is a condition selected from the group consisting of sepsis, severe sepsis, septicaemia, septic shock, disseminated intravascular coagulation (DIC), and systemic inflammatory response syndrome (SIRS).

6. A method according to claim 5 wherein said condition is DIC.

* * * * *